US008835619B2

(12) United States Patent
Levis et al.

(10) Patent No.: US 8,835,619 B2
(45) Date of Patent: Sep. 16, 2014

(54) **HEAT SHOCK PROTEINS FROM *MYCOBACTERIUM LEPRAE* AND USES THEREOF**

(75) Inventors: William R. Levis, New York, NY (US); Frank T. Martiniuk, Wood-Ridge, NJ (US)

(73) Assignee: New York University, New York, NY (US)

(*) Notice: Subject to any disclaimer, the term of this patent is extended or adjusted under 35 U.S.C. 154(b) by 1111 days.

(21) Appl. No.: 12/624,288

(22) Filed: Nov. 23, 2009

(65) Prior Publication Data

US 2010/0136016 A1 Jun. 3, 2010

Related U.S. Application Data

(62) Division of application No. 11/523,215, filed on Sep. 29, 2006, now Pat. No. 7,622,121.

(60) Provisional application No. 60/719,163, filed on Sep. 21, 2005.

(51) Int. Cl.

| | |
|---|---|
| ***C07H 21/04*** | (2006.01) |
| ***A61K 39/04*** | (2006.01) |
| ***G01N 33/569*** | (2006.01) |
| ***C07K 16/12*** | (2006.01) |
| ***C07K 14/35*** | (2006.01) |
| *A61K 39/00* | (2006.01) |

(52) U.S. Cl.

CPC ............ *G01N 33/5695* (2013.01); *A61K 39/00* (2013.01); *A61K 2039/6043* (2013.01); *C07K 16/1289* (2013.01); *A61K 2039/505* (2013.01); *C07K 14/35* (2013.01)

USPC ... 536/23.7; 536/23.4; 435/253.1; 424/200.1; 424/248.1

(58) Field of Classification Search

None

See application file for complete search history.

(56) References Cited

U.S. PATENT DOCUMENTS

| | | | |
|---|---|---|---|
| 4,237,224 | A | 12/1980 | Cohen et al. |
| 5,232,833 | A | 8/1993 | Sanders et al. |
| 5,464,750 | A | 11/1995 | Sanders et al. |
| 5,780,034 | A | 7/1998 | Cohen et al. |
| 5,780,246 | A | 7/1998 | Sanders et al. |
| 5,807,690 | A | 9/1998 | Sanders et al. |
| 6,007,821 | A | 12/1999 | Srivastava et al. |
| 6,214,341 | B1 | 4/2001 | Thomas, Jr. et al. |
| 6,475,490 | B1 | 11/2002 | Srivastava et al. |
| 6,495,347 | B1 | 12/2002 | Siegel et al. |
| 6,497,880 | B1 | 12/2002 | Wisniewski |
| 6,524,584 | B2 | 2/2003 | Kensil |
| 6,524,825 | B1 | 2/2003 | Mizzen et al. |
| 6,610,659 | B1 | 8/2003 | Pramod |
| 6,645,495 | B1 | 11/2003 | Kensil et al. |
| 6,657,055 | B2 | 12/2003 | Siegel et al. |
| 6,797,480 | B1 | 9/2004 | Srivastava |
| 6,797,491 | B2 | 9/2004 | Neefe et al. |
| 6,900,035 | B2 | 5/2005 | Mizzen et al. |
| 6,921,534 | B2 | 7/2005 | Mizzen et al. |
| 2003/0050469 | A1 | 3/2003 | Siegel et al. |
| 2003/0099664 | A1 | 5/2003 | Wisniewski |
| 2003/0148456 | A1 | 8/2003 | Mizzen et al. |
| 2003/0170268 | A1 | 9/2003 | Neefe et al. |
| 2004/0235741 | A1 | 11/2004 | Neefe et al. |
| 2005/0037017 | A1 | 2/2005 | Mizzen et al. |
| 2005/0089841 | A1 | 4/2005 | Siegel et al. |
| 2005/0152917 | A1 | 7/2005 | Mizzen et al. |
| 2005/0176672 | A1 | 8/2005 | Scheule et al. |
| 2005/0202044 | A1 | 9/2005 | Mizzen et al. |

FOREIGN PATENT DOCUMENTS

| | | |
|---|---|---|
| EP | 0534858 | 3/1993 |
| WO | WO 03/058248 | 7/2003 |
| WO | WO03058248 A2 * | 7/2003 |
| WO | WO03062470 A1 * | 7/2003 |
| WO | WO 2005/025612 | 3/2005 |

OTHER PUBLICATIONS

Chu et al. Clin Exp Immul 2000; vol. 121 pp. 216-225.*

Botstein et al., "Construction of a Genetic Linkage Map in Man Using Restriction Fragment Length Polymorphisms," *Am. J. Hum. Genet.* 32:314-331 (1980).

Cole et al., "Massive Gene Decay in Leprosy *Bacillus*" *Nature* 409:1007-11 (2001).

Groathouse et al., "Multiple Polymorphic Loci for Molecular Typing of Strains of *Mycobacterium leprae*," *J. Clin. Micro* 42:1666-1672 (2004).

Kang et al., "Differential Production of Interleukin-10 and Interleukin-12 in Mononuclear Cells from Leprosy Patients with a Toll-Like Receptor 2 Mutation," *Immunology* 112:674-680, (2004).

Kurucz et al., "Ultrastructural Localization of Hsp-72 Examined with a New Polyclonal Antibody Raised Against the Truncated Variable Domain of the Heat Shock Protein," *Cell Stress & Chaperones* 4(2):139-152 (1999).

Genbank Accession No. Q546M0 (Sep. 13, 2005) [Retrieved on Jun. 26, 2007 retrieved from: <url:http://www.ncbi.nlm.nih.gov/entrez/viewer.fcgi?db=Protein&id=75504587>].

Oliveira et al., "Expression of Toll-like Receptor 2 on Human Schwann Cells: A Mechanism of Nerve Damage in Leprosy," *Infection and Immun.* 71:1427-1433 (2003).

(Continued)

*Primary Examiner* — Padma V Baskar

(74) *Attorney, Agent, or Firm* — LeClairRyan, a Professional Corporation

(57) ABSTRACT

The present invention is directed to heat shock proteins from *Mycobacterium leprae* as well as their encoding polynucleotides and vectors and host cells containing these polynucleotides. These heat shock proteins and their encoding polynucleotides are useful in detection of *Mycobacterium leprae*. In addition, the heat shock protein can be used as an adjuvant in a pharmaceutical composition containing an antigen to induce or enhance the immune response against the antigen. Further, the heat shock protein may be used to treat atopic conditions or as a vaccine against *Mycobacterium leprae*. Alternatively, the heat shock protein can be used to form a fusion protein with an antigen to induce or enhance the immune response against the antigen.

7 Claims, 13 Drawing Sheets

(56) References Cited

OTHER PUBLICATIONS

Rastogi et al., "Species Specific Identification of *Mycobacterium leprae* by PCR-Restriction Fragment Length Polymorphism Analysis of the *hsp65* Gene," *J. Clinical Microbiology* 37:2016-2019 (1999).

Ruiz et al., "Amplified-Fragment Length Polymorphism as a Complement to IS*6110*-Based Restriction Fragment Length Polymorphism Analysis for Molecular Typing of *Mycobacterium tuberculosis," J. Clin Micro* 41(10):4820-4822 (2003).

Sasaki et al., "*Mycobacterium leprae* and Leprosy: A Compendium," *Microbiol. Immunol* 45(10):729-36 (2001).

Shin et al., "Variable Numbers of TTC Repeats in *Mycobacterium leprae* DNA from Leprosy Patients and Use in Strain Differentiation," *J. Clinical Microbiology* 38(12):4535-4538 (2000).

Truman et al., "Genotypic Variation and Stability of Four Variable-Number Tandem Repeats and Their Suitability for Discriminating Strains of *Mycobacterium leprae," J. Clinical. Micro* 42(6):2558-2565 (2004).

Vos et al., "AFLP: A New Technique for DNA Fingerprinting," *Nucleic Acids Res*. 23(21):4407-4414 (1995).

Welsh et al., "Fingerprinting Genomes Using PCR with Arbitrary Primers," *Nucleic Acids Res*. 18(24):7213-7218 (1990).

Williams et al., "DNA Polymorphism Amplified by Arbitrary Primers are Useful as Genetic Markers," *Nucleic Acids Res*. 18(22):6531-6535 (1990).

Young et al., "Leprosy, Tuberculosis, and the New Genetics," *J. Bacteriology*. 175:1-6 (1993).

Brunello et al., *Journal of Clinical Microbiology* 39:2799-2806 (2001).

Greenspan et al., *Nature Biotechnology* 7:936-937 (1999).

Bowie et al., *Science* 247:1306-1310 (1990).

Plotkin et al., *Vaccines* W.B. Saunders Company, p. 571 (1988).

Burgess et al., *The Journal of Cell Biology* 111:2129-2138 (1990).

Leao et al., "Multicenter Evaluation of Mycobacteria Identification by PCR Restriction Enzyme Analysis in Laboratories from Latin America and the Caribbean," J. Microbiol. Methods 61:193-199 (2005).

* cited by examiner

% amino acid variation from published sequence

| | | |
|---|---|---|
| Clone 3a | 7/112 | = 6.2% |
| 3b | 10/112 | = 8.9% |
| 3c | 5/112 | = 4.5% |
| 3e | 15/112 | = 13.4% |
| 3f | 10/112 | = 8.9% |
| 11a | 18/112 | = 16.1% |
| 11b | 40/112 | = 35.7% |
| 11e | 30/112 | = 26.8% |

Combining all clones changes 92/112 amino acids or 82%x published amino acid sequence on top vs. clones 3a,b,c,e,f,11a,b,e (in order) number = amino acid Bold = differences

1- Glu Lys Ile Gly Ala
E K I G A
Glu Lys Ile Gly Ala
E K I G A
Glu Lys Ile Gly Ala
E K I G A
Glu Lys Ile Gly Ala
E K I G A
Glu Lys Ile Gly Ala
E K I G A
Glu Lys Ile Gly Ala
E K I G A
Glu Lys Ile Gly Ala
E K I G A
Glu Lys Ile Gly Ala
E K I G A
Glu Lys Ile Gly Ala
E K I G A

FIGURE 1A

6- Glu Leu Val Lys Glu Val Ala Lys Lys Thr
E L V K E V A K K T
Glu Leu Val Lys Glu Val Ala Lys Lys Thr
E L V K E V A K K T
Glu Leu Val Lys Glu Val Ala Lys Lys Thr
E L V K E V A K K T
Glu Leu Val Lys Glu Val Ala Lys Lys Thr
E L V K E V A K K T
Glu Leu Val Lys Glu Val Ala Lys Lys Thr
E L V K E V A K K T
Asp Asp Val Ala Gly Asp Gly Thr Thr Thr
D D V A G D G T T T
Glu Leu Val Lys Glu Val Ala Lys Lys Thr
E L V K E V A K K T
Glu Leu Val Lys Glu Ala Ala Lys Lys Thr
E L V K E A A K K T
Glu Leu Val Lys Glu Val Ala Lys Lys Thr
E L V K E V A K K T

16- Asp Asp Val Ala Gly Asp Gly Thr Thr Thr
D D V A G D G T T T
Asp Asp Val Ala Gly Asp Gly Thr Thr Thr
D D V A G D G T T T
Asp Asp Val Ala Gly Asp Gly Thr Thr Thr
D D V A G D G T T T
Asp Asp Val Ala Gly Asp Gly Thr Thr Thr
D D V A G D G T T T
Asp Asp Val Ala Gly Asp Gly Thr Thr Thr
D D V A G D G T T T
Asp Asp Val Ala Gly Asp Gly Thr Thr Thr
D D V A G D G T T T
Asp Glu Val Ala Cys Asp Gly Thr Thr Thr
D E V A C D G T T T
Asp Glu Val Ala Gly Asp Gly Thr Thr Thr
D E V A G D G T T T
Asp Glu Val Ala Gly Asp Gly Thr Thr Thr
D E V A G D G T T T

FIGURE 1B

| | | | | | | | | | | |
|---|---|---|---|---|---|---|---|---|---|---|
| 26- | Ala | Thr | Val | Leu | Ala | Gln | Ala | Leu | Val | Lys |
| | A | T | V | L | A | Q | A | L | V | K |
| | Ala | Thr | Val | Leu | Ala | Gln | Ala | Leu | Val | Lys |
| | A | T | V | L | A | Q | A | L | V | K |
| | Ala | Thr | Val | Leu | Ala | Gln | Ala | Leu | Val | **Arg** |
| | A | T | V | L | A | Q | A | L | V | **R** |
| | Ala | Thr | Val | Leu | Ala | Gln | Ala | Leu | Val | Lys |
| | A | T | V | L | A | Q | A | L | V | K |
| | Ala | Thr | Val | Leu | Ala | Gln | Ala | Leu | Val | Lys |
| | A | T | V | L | A | Q | A | L | V | K |
| | Ala | Thr | Val | Leu | Ala | Gln | Ala | Leu | Val | Lys |
| | A | T | V | L | A | Q | A | L | V | K |
| | Ala | Thr | Val | Leu | Ala | Gln | Ala | Leu | Val | **Arg** |
| | A | T | V | L | A | Q | A | L | V | **R** |
| | Ala | Thr | Val | Leu | Ala | Gln | Ala | Leu | Val | **Arg** |
| | A | T | V | L | A | Q | A | L | V | **R** |
| | Ala | Thr | Val | Leu | Ala | Gln | Ala | Leu | **Asp** | **Arg** |
| | A | T | V | L | A | Q | A | L | **D** | **R** |

| | | | | | | | | | | |
|---|---|---|---|---|---|---|---|---|---|---|
| 36- | Glu | Gly | Leu | Arg | Asn | Val | Ala | Ala | Gly | Ala |
| | E | G | L | R | N | V | A | A | G | A |
| | Glu | Gly | Leu | Arg | Asn | Val | Ala | Ala | Gly | Ala |
| | E | G | L | R | N | V | A | A | G | A |
| | Glu | Gly | Leu | Arg | Asn | Val | Ala | Ala | Gly | Ala |
| | E | G | L | R | N | V | A | A | G | A |
| | Glu | Gly | Leu | Arg | Asn | Val | Ala | Ala | Gly | Ala |
| | E | G | L | R | N | V | A | A | G | A |
| | Glu | Gly | Leu | Arg | Asn | Val | Ala | Ala | Gly | Ala |
| | E | G | L | R | N | V | A | A | G | A |
| | Glu | Gly | Leu | Arg | Asn | Val | Ala | Ala | Gly | Ala |
| | E | G | L | R | N | V | A | A | G | A |
| | Glu | Gly | Leu | Arg | Asn | Val | Ala | Ala | Gly | Ala |
| | E | G | L | R | N | V | A | A | G | A |
| | Glu | Gly | Leu | Arg | Asn | Val | Ala | Ala | Gly | Ala |
| | E | G | L | R | N | V | A | A | G | A |
| | Glu | Gly | Leu | Arg | Asn | Val | Ala | Ala | Gly | Ala |
| | E | G | L | R | N | V | A | A | G | A |

FIGURE 1C

46- Asn Pro Leu Gly Leu Lys Arg Gly Ile Glu
N P L G L K R G I E
Asn Pro Leu Gly Leu Lys Arg Gly Ile Glu
N P L G L K R G I E
Asn Pro Leu Gly Leu Lys Arg Gly Ile Glu
N P L G L K R G I E
Asn Pro Leu Gly Leu Lys Arg Gly Ile Glu
N P L G L K R G I E
Asn Pro Leu Gly Leu Lys Arg Gly Ile Glu
N P L G L K R G I E
Asp Pro Leu Ser Leu Lys Arg Gly Ile Glu
D P L S L K R G I E
Asp Pro Leu Ser Leu Lys Arg Gly Ile Glu
D P L S L K R G I E
Asp Pro Leu Ser Leu Lys Arg Gly Ile Glu
D P L S L K R G I E

56- Lys Ala Val Asp Lys Val Thr Glu Thr Leu
K A V D K V T E T L
Lys Ala Val Asp Lys Ile Thr Gln Thr Leu
K A V D K I T Q T L
Lys Ala Val Gly Lys Ile Thr Glu Val Leu
K A V G K I T E V L
Lys Ala Val Asp Lys Ile Thr Gln Thr Leu
K A V D K I T Q T L
Lys Ala Val Asp Lys Ile Thr Gln Thr Leu
K A V D K I T Q T L
Asn Pro Leu Gly Leu Lys Arg Gly Ile Glu
N P L G L K R G I E
Lys Ala Val Ala Ala Val Thr Glu Gln Leu
K A V A A V T E Q L
Lys Ala Val Ala Ala Val Thr Glu Gln Leu
K A V A A V T E Q L
Lys Ala Val Ala Ala Val Thr Glu Gln Leu
K A V A A V T E Q L

FIGURE 1D

66- Leu Lys Asp Ala Lys Glu Val Glu Thr Lys
L K D A K E V E T K
Leu Asp Ser Ala Lys Asp Val Glu Thr Lys
L D S A K D V E T K
Leu Ser Ser Ala Lys Asp Val Glu Thr Lys
L S S A K D V E T K
Leu Asp Ser Ala Lys Asp Val Glu Thr Lys
L D S A K D V E T K
Leu Asp Ser Ala Glu Asp Val Glu Thr Lys
L D S A E D V E T K
Leu Asp Pro Ala Lys Asp Val Glu Thr Lys
L D P A K D V E T K
Leu Ala Ser Ala Lys Glu Val Glu Thr Lys
L A S A K E V E T K
Leu Ala Ser Ala Lys Glu Val Glu Thr stop
L A S A K E V E T stop
Leu Ala Ser Ala Lys Glu Val Glu Thr Lys
L A S A K E V E T K 76- Glu Gln Ile Ala Ala Thr Ala Ala Ile Ser
E Q I A A T A A I S
Glu Gln Ile Ala Ala Thr Ala Ser Ile Ser
E Q I A A T A S I S
Glu Gln Ile Ala Ala Thr Ala Gly Ile Ser
E Q I A A T A G I S
Glu Gln Ile Ala Ala Thr Ala Ala Ile Ser
E Q I A A T A A I S
Glu Gln Ile Ala Ala Thr Ala Gly Ile Pro
E Q I A A T A G I P
Glu Gln Ile Ala Ala Thr Ala Gly Thr Ser
E Q I A A T A G T S
Glu Ala Ile Ala Ala Thr Ala Ser Ile Ser
E E I A A T A S I S
- - - - - - - - - -
Glu Glu Ile Ala Ala Thr Ala Ser Ile Ser
E E I A A T A S I S

FIGURE 1E

86- Ala Gly Asp Gln Ser Ile Gly Asp Leu Ile
A G D Q S I G D L I
Ala Gly Asp Gln Ser Ile Gly Asp Leu Ile
A G D Q S I G D L I
Ala Gly Asp Gln Ser Ile Gly Asp Leu Ile
A G D Q S I G D L I
Ala Gly Asp Gln Ser Ile Gly Asp Leu Ile
A G D Q S I G D L I
Ala Gly Asp Gln Ser Ile Gly Asp Leu Ile
A G D Q S I G D L I
Ala Gly Asp Gln Ser Ile Gly Asp Pro Ile
A G D Q S I G D P I
Ala Ala Asp Thr Gln Ile Gly Ala Leu Ile
A A D T Q I G A L I
- - - - - - - - - -
Ala Ala Asp Thr Gln Ile Gly Ala Leu Ile
A A D T Q I G A L I

96- Ala Glu Ala Met Asp Lys Val Gly Asn Glu
A E A M D K V G N E
Ala Glu Ala Lys Asp Lys Val Gly Asn Glu
A E A K D K V G N E
Ala Val Ala Met Asp Lys Val Gly Asn Glu
A V A M D K V G N E
Ala Glu Ala Met Asp Lys Val Gly Asn Glu
A E A M D K V G N E
Ala Glu Ala Met Asp Lys Val Gly Asn Gly
A E A M D K V G N G
Ala Glu Ala Met Asp Gly Val Gly Asn Glu
A E A M D E V G N E
Ala Glu Ala Leu Asp Lys Val Gly Lys Glu
A E A L D K V G K E
- - - - - - - - - -
Ala Glu Ala Leu Asp stop - - - -
A E A L D stop

FIGURE 1F

106- Gly Val Ile Thr Val Glu Glu Ser- 113
G V I T V E E S
Gly Val Ile Thr Val Glu Glu Ser
G V I T V E E S
Gly Ile Ile Thr Val Glu Glu Ser
G I I T V E E S
Gly Val Ile Thr Val Glu Glu Ser
G V I T V E E S
GCG TCA TCA CCG TCG AGG AGT CC
Ala Ser Ser Pro Ser Arg Ser
A S S P S R S
Gly Val Ile Thr Val Glu Glu Ser
G V I T V E E S
Gly Val Ile Thr Val Glu Glu Ser
G V I T V E E S
\- - - - - - - -
\- - - - - - - -

FIGURE 1G

% variation compared to published nucleotide sequence

| | | |
|---|---|---|
| Clone | 3a | 53/339 = 15.6% |
| | 3b | 55/339 = 16.2% |
| | 3c | 48/339 = 14.2% |
| | 3e | 52/339 = 15.3% |
| | 3f | 50/339 = 14.8% |
| | 11a | 79/339 = 23.3% |
| | 11b | 82/339 = 24.2% |
| | 11e | 76/339 = 22.4% |

Combination all variation 142/339 = 41.9%

*Published nucleotide sequence-lower case on top vs. clones 3a,b,c,e,f,11a,b,e-caps (in order); differences in bold*

1- gag aag att ggc gct
GAG AAG ATC GGC GCC
GAG ACG ATC GGC GCC
GAG AAG ATC GGC GCC
GAG AAG ATC GGC GCC
GAG AAG ATC GGC GCC
GAG AAG ATC GGC GCC
GAG AAG ATC GGC GCC
GAG GAG ATC GGC GCC

FIGURE 2A 16- gag ttg gtc aag gaa gtc gcc aag aag aca
GAG CTG GTC AAG GAA GTC GCC AAG AAG ACC
GAG CTG GTC AAG GAA GTC GCC AAG AAG ACC
GAG CTG GTC AAG GAA GTC GCC AAG AAG ACC
GAG CTG GTC AAG GAA GTC GCC AAG AAG ACC
GAG CTG GTC AAG GAA GTC GCC AAG AAG ACC
GAG CTG GTC AAG GAA GTC GCC AAG AAG ACT
GAG CTG GTC AAG GAA GCC GCC AAG AAG ACT
GAG CTG GTC AAG GAA GTC GCC AAG AAG ACT

46- gat gac gtc gcc ggt gat ggc acc acg acg
GAC GAC GTC GCC GGT GAC GGC ACC ACG ACG
GAC GAC GTC GCC GGT GAC GGC ACG ACG ACG
GAG CTG GTC AAG GAA GTC GCC AAG AAG ACC
GAC GAC GTC GCC GGT GAC GGC ACG ACG ACG
GAC GAC GTC GCC GGT GAC GGC ACC ACG GCG
GAC GAA GTC GCC TGC GAC GGT ACC ACC ACC
GAC GAA GTC GCC GGC GAC GGT ACC ACC ACC
GAC GAA GTC GCC GGC GAC GGT ACC ACC ACC

76- gcc acc gtg ctg gcc cag gca ttg gtc aaa
GCC ACC GTG CTG GCC CAG GCC CTG GTC AAA
GCC ACG GTG CTC GCC CAG GCG TTG GTC CGC
GCC ACC GTG CTG GCC CAG GCC CTG GTT AAA
GCC ACG GTT CTG GCC CAG GCC TTG GTC CGC
GCC ACC GTG CTG GCC CAG GCC CTG GTC AAA
GCT ACC GTT CTG GCC CAG GCC TTG GTT CGC
GCT ACC GTT CTG GCC CAG GCC TTG GTT CGC
GCT ACC GTT CTG GCC CAG GCC TTG GAT CGC

FIGURE 2B 106- gag ggc cta cgc aac gtc gcg gcc ggc gcc
GAG GGT CTG CGT AAC GTT GCT GCG GGC GCC
GAG GGC CTG CGC AAC GTC GCG GCT GGC GCC
GAG GGT CTG CGT AAC GTT GCT GCG GGC GCC
GAG GGC CTG CGT AAC GTC GCC GCC GGC GCC
GAG GGT CTG CGT AAC GTT GCT GCG GGC GCC
GAA GGC TTG CGC AAC GTC GCA GCC GGC GCT
GAA GGC TTG CGC AAC GTC GCA GCC GGC GCT
GAA GGC TTG CGC AAC GTC GCA GCC GGC GCT 136- aac ccg cta ggt ctc aag cgt ggc atc gag
AAC CCA CTG GGT CTG AAG CGC GGC ATC GAG
AAC CCG CTG GGT CTC AAG CGC GGC ATC GAG
AAC CCG CTG GGT CTG AAG CGC GGC ATC GAG
AAC CCG CTG GGT CTG AAG CGC GGC ATC GAG
AAC CCG CTG GGT CTG AAG CGC GGC ATC GAG
GAT CCG CTG AGC CTC AAG CGC GGC ATC GAG
GAT CCG CTG AGC CTC AAG CGC GGC ATC GAG
GAT CCG CTG AGC CTC AAG CGC GGC ATC GAG 166- aaa gct gtc gat aag gta act gag act ctg
AAG GCC GTC GAT AAG ATC ACC CAG ACG CTG
AAG GCC GTT GGA AAA ATC ACG GAA GTT CTC
AAG GCC GTC GAT AAG ATC ACC CAG ACG CTG
AAG GCC GTC GAT AAG ATC ACC CAG ACG CTG
AAG GCC GTC GAT AAG ATC ACC CAG ACG CTG
AAG GCT GTC GCC GCG GTG ACC GAG CAG CTG
AAG GCT GTC GCC GCG GTG ACC GAG CAG CTG
AAG GCT GTC GCC GCG GTG ACC GAG CAG CTG

FIGURE 2C 196- ctc aag gac gct aag gag gtc gaa acc aag
CTG GAC TCG GCC AAG GAC GTC GAG ACC AAG
CTG TCG TCG GCC AAG GAC GTC GAG ACC AAG
CTG GAC TCG GCC AAG GAC GTC GAG ACC AAG
CTG GAC TCG GCC GAG GAC GTC GAG ACC AAG
CTG GAC CCG GCC AAG GAC GTC GAG ACC AAG
CTG GCT TCC GCC AAG GAA GTC GAG ACC AAA
CTG GCT TCC GCC AAG GAA GTC GAG ACC TAA
CTG GCT TCC GCC AAG GAA GTC GAG ACC AAA 226- gaa caa att gct gcc act gca gcg att tcg
GAG CAG ATC GCA GCC ACC GCT AGC ATT TCT
GAG CAG ATC GCT GCC ACC GCT GGC ATT TCT
GAG CAG ATC GCT GCC ACC GCG GCC ATC TCC
GAG CAG ATC GCT GCC ACC GCT GGC ATT CCT
GAG CAG ATC GCT GCC ACC GCT GGC ACA TCA
GAA GAG ATC GCG GCC ACT GCT TCG ATC TCC
GAA GAG ATC GCG GCC ACT GCT TCG ATC TCC
GAA GAG ATC GCG GCC ACT GCT TCG ATC TCC 256- gcg ggt gac cag tcg atc ggt gat ctg atc
GCC GGT GAC CAG TCG ATC GGC GAC CTG ATC
GCC GGT GAC CAG TCG ATC GGC GAC CTG ATC
GCG GGC GAC CAG TCT ATC GGC GAC CTG ATC
GCC GGT GAC CAG TCG ATC GGC GAC CTG ATC
GCC GGT GAC CAG TCG ATC GGC GAC CCG ATC
GCC GCG GAC ACC CAG ATC GGC GCG TTG ATC
GCC GCG GAC ACC CAG ATC GGC GCG TTG ATC
GCC GCG GAC ACC CAG ATC GGC GCG TTG ATC

FIGURE 2D 286- gcc gag gcg atg gac aag gtt ggc aac gag
GCC GAA GCG AAG GAC AAG GTC GGC AAC GAG
GCC GTA GCG ATG GAC AAG GTC GGC AAC GAG
GCC GAG GCG ATG GAC AAG GTC GGC AAC GAG
GCC GAA GCG ATG GAC AAG GTC GGC AAC G_G
GCC GAA GCG ATG GAC GAG GTC GGC AAC GAG
GCC GAA GCC CTG GAC AAG GTC GGC AAA GAA
GCC GAA GCC CTG GAC AAG GTC GGC AAA GAA
GCC GAA GCC CTG GAC TAG GTC GGC AAA GAA 316- ggt gtt atc acc gtc gag gaa tcc
GGC GTC ATC ACC GTC GAG GAG TCC
GGC ATC ATC ACC GTC GAG GAG TCC
GGC GTC ATC ACC GTC GAG GAG TCC
GGC GTC ATC ACC GTC GAG GAG TCC
GGC GTC ATC ACC GTC GAG GAG TCC
GGC GTC ATC ACG GTC GAA GAG TCC
GGC GTC ATC ACG GTC GAA GAG TCC
GGC GTC ATC ACG GTC GAA GAG TCC

FIGURE 2E

HEAT SHOCK PROTEINS FROM *MYCOBACTERIUM LEPRAE* AND USES THEREOF

This application is a division of U.S. patent application Ser. No. 11/523,215, filed Sep. 19, 2006, which claims the benefit of U.S. Provisional Patent Application Ser. No. 60/719,163, filed Sep. 21, 2005, each of which is hereby incorporated by reference in its entirey.

The subject matter of this application was made with support from the United States Government under GCRC NIH Grant No. M01 RR00096. The U.S. Government has certain rights in this invention.

FIELD OF THE INVENTION

The present invention is directed to heat shock proteins from *Mycobacterium leprae* and uses thereof.

BACKGROUND OF THE INVENTION

Leprosy or Hansen's disease is a chronic infectious disease that primarily affects the skin, peripheral nerves, upper respiratory tract and eyes (Sasaki et al., "*Mycobacterium leprae* and Leprosy: A Compendium," *Microbiol. Immunol* 45:729-36 (2001)). The pathogen is an acid-fast bacillus, *Mycobacterium leprae* (*M. leprae*), that was first identified by the Norwegian physician, Gerhard Hansen in 1873. The bacilli proliferate in macrophages infiltrating the skin and gain entry to the dermal nerves via the laminar surface of Schwann cells where they replicate. After entry, the Schwann cells proliferate and then die. Combined with the ensuing host inflammatory response to the mycobacteria, damage results in the peripheral nerves which leads to functional impairment, including desensitization to temperature, light touch and pain. It appears that attachment to Schwann cells causes demyelination and proliferation of large numbers of mycobacterium in the cells (Rambukkana et al., "Contact Dependent Demyelation by *Mycobacterium Leprae* in the Absence of Immune Cells," *Science* 296:927-931 (2002), Oliveira et al., "Expression of Toll-like Receptor 2 on Human Schwann Cells: A Mechanism of Nerve Damage in Leprosy," *Infection and Immun.* 71:1427-1433 (2003), Kim et al., "Detection of Gene Mutations Related with Drug Resistance in *Mycobacterium leprae* from Leprosy Patients Using Touch-Down (TD) PCR," *FEMS Immunology and Medical Microbiology* 36:27-32 (2003)).

Leprosy currently remains endemic in some developing parts of the world (Ishii et al, "Survey of Newly Diagnosed Leprosy Patients in Native and Foreign Residents of Japan" *Int. J. Lepr.* 68:172-6 (2000)). The WHO in 1991 wanted to eliminate leprosy by 2000 (World Health Organization. "World Health Assembly-Resolution," WHA44.9 (1991)) (less than 1 case per 10,000). By 2000, 597,232 cases were registered and 719,330 cases were newly detected (World Health Organization. "Leprosy-Global Situation," *Weekly Epidemiological Record* 75:225-232 (2000)). There have been 690,830 newly detected patients in 2001 with 91% in the top six countries where the disease is most prevalent. The prevalence rate in these top six countries has been estimated at 3.9 per 10,000, with a very uneven distribution. By 2001, India accounted for 78% (439,782 cases, 4.3 per 10,000), Brazil-12% (77,676 cases, 4.5 per 10,000), Nepal-1.7% (10, 657 cases, 4.4 per 10,000), Myanmar-1.5% (8,237 cases, 1.8 per 10,000), Mozambique-1% (6,775 cases, 3.4 per 10,000) and Angola-0.6% (4,115 cases, 3.1 per 10,000). The diagnosis of leprosy is mainly based on the clinical signs and the symptoms of the disease, plus the results of skin smears. Patients showing negative smears at all sites are grouped as paucibacillary leprosy (PB), while those showing positive smears at any site are multibacillary leprosy (MB). The clinical classification also uses the number of skin lesions and nerves involved as the basis for grouping leprosy patients into PB and MB leprosy and to determine the treatment regimen (Ridley et al., "Classification of Leprosy According to Immunity—A Five Group System," *Int. J. Lepr.* 54:255-73 (1966)). Bleharski et al. (Bleharski et al., "Use of Genetic Profiling in Leprosy to Discriminate Clinical Forms of the Disease," *Science* 301:1527-1530 (2003)) using genetic expression profiling were able to correlate gene expression with clinical forms of leprosy. They found significant expression of leukocyte immunoglobulin-like receptor (LIR) genes in lepromatous leprosy and increased expression of Toll-like receptor 2 and 1 (LTRs) in tuberculoid leprosy (Krutzik et al., "Activation and Regulation of Toll-Like Receptors 2 and 1 in Human Leprosy," *Nature Medicine* 9:525-532 (2003), Krutzik et al., "The Role of Toll-Like Receptors in Combating Mycobacteria," *Seminars in Immunology* 16:35-41 (2004))

There are several effective chemotherapeutic agents against *M. leprae*. Dapsone (diaphenylsulfone, DDS), rifampicin, clofazimine, ofloxacin and minocycline constitute the multidrug therapy (MDT) regimen. Other effective chemotherapeutic agents include levofloxacin, sparfloxacin and clarithromycin (Sugita et al, "A Case of Relapsed Leprosy Successfully Treated with Sparfloxacin," *Arch. Deunatol* 32:1397-1398 (1996), Ishii et al., "Sparfloxacin in the Treatment of Leprosy Patients," *Int. J. Dermatol* 36:619-62 (1997), WHO. "Model Prescribing Information-Drug Used in Leprosy," WHO/DMP/DSI/98.1 (1998), WHO. "Chemotherapy of Leprosy for Control Programmes," *WHO Technical report series* 675 (1982), WHO. "WHO Expert Committee on Leprosy, Sixth Report," *WHO Technical report series* 768 (1988), WHO. "Chemotherapy of Leprosy, Report of a WHO Study Group," WHO Technical report series 847 (1994), WHO. "A Guide to Eliminating Leprosy as a Public Health Problem," WHO/LEP/95.1 (1995), WHO. "WHO Expert Committee on Leprosy, Seventh Report," *Technical report series* 874 (1998)). It has been proven that monotherapy will result in the development of resistance to the drug. Trials have shown that complete clearing of lesions takes 1-2 years after treatment discontinuation. There is evidence that 3-6 months of administration of MDT clears all live organisms. Resistance of *M. leprae* to anti-leprosy drugs has been reported world-wide. Drug resistance is due to genetic changes in drugs targeting genes for rifampicin (rpoB or β-subunit of RNA polymerase), dapsone (folP or dihydropteroate synthase), and ofloxacin (gyrA or DNA gyrase) (Williams et al., "PCR-Based Diagnosis of Leprosy in the United States," *Clin. Micro. Newsletter* 25:57-61 (2003), You et al., "Mutations in Genes Related to Drug Resistance in *Mycobacterium Leprae* Isolates from Leprosy Patients in Korea," *J. Medicine* 50:6-11 (2005), Maeda et al., "Multidrug Resistant *Mycobacterium Leprae* from Patients with Leprosy," *Antimicrobial Agents and Chemotherapy* 45:3636-3639 (2001)). Patients with the tuberculoid type are relatively resistant to the pathogen with localized lesions that express the type-1 cytokines characteristic of cell-mediated immunity. Lepromatous leprosy is relatively susceptible to the organism with systemically disseminated and type-2 cytokines characteristic of humoral responses (WHO. "Chemotherapy of Leprosy for Control Programmes," *WHO Technical Report Series* 675 (1982), Kang et al., "Differential Production of Interleukin-10 and Interleukin-12 in Mononuclear Cells from Leprosy Patients with a Toll-Like Receptor 2 Mutation. Immunology," 112:674-680, (2004)).

Examining the genetic diversity of *M. leprae* is only at its infancy. In comparison to the *M. tuberculosis* genome, the *M. leprae* genome is smaller; has less G/C content; less protein-coding genes; more gene density and similar average gene length (Cole et al., "Massive Decay in Leprosy Bacillus" *Nature* 409:1007-11 (2001), Kato-Maeda et al., "Comparing Genomes Within the Species *Mycobacterium Tuberculosis,*" *Genome Research* 11:547-554 (2001), Rambukkana, A. "*M. Leprae* Genome Sequence," *Trends in Microbology* 98:157 (2001)). There has been little evidence for deletion events or insertions as the cause of the smaller size in the *M. leprae* genome. Genetic diversity has been found for short tandem repeat loci. These include the TIC repeat of 10-37 repeats between two pseudogenes, a 6 bp (GACATC) repeat in the rpoT gene (3 or 4 repeats in Asia) and two newly described TA and AT repeats (Shin et al., "Variable Numbers of TTC Repeats in *Mycobacterium Leprae* DNA from Leprosy Patients and Use in Strain Differentiation," *J. Clinical Microbiology* 38:4535-4538 (2000), Chae et al., "Typing of Clinical Isolates of *Mycobacterium Leprae* and Their Distribution in Korea," *Leprosy Review* 73:41-46 (2002), Young, D. "Prospects for Molecular Epidemiology of Leprosy," *Leprosy Review.* 74:11-17 (1993), Young et al., "Leprosy, Tuberculosis, and the New Genetics," *J. Bacteriology.* 175:1-6 (1993), Cole et al., "Repetitive Sequences in *Mycobacterium Leprae* and Their Impact on Genome Plasticity," *Leprosy Review* 72:449-461 (2001), Matsuoka et al., "*Mycobacterium Leprae* Typing by Genomic Diversity and Global Distribution of Genotypes," *International J. Leprosy* 68:121-128 (2000)). Groathouse et al. (Groathouse et al., "Multiple Polymorphic Loci for Molecular Typing of Strains of *Mycobacterium Leprae,*" *J. Clin. Micro* 42:1666-1672 (2004)) have identified nine other potential short tandem repeats (STRs). Conclusive identification of the presence of *M. leprae* in a sample can be obtained by PCR-restriction fragment length polymorphism analysis of the heat shock 65 gene (hsp65) by digestion with BstEII and/or HaeIII followed by Polyacrylamide Gel Electrophoresis (PAGE) (Rastogi et al., "Species Specific Identification of *Mycobacterium Leprae* by PCR-Restriction Fragment Length Polymorphism Analysis of the Hsp65 Gene," *J. Clinical Microbiology* 37:2016-2019 (1999)). Molecular epidemiology will make it possible to study the global and geographical distributions of *M. leprae*, explore the relationship between genotypes-incidence rates, mode of transmission and the type of disease (tuberculoid versus lepromatous). Cole et al., "Massive Decay in *Leprosy Bacillus", Nature* 409:1007-1011 (2001). However, to date no methods are available for performing molecular epidemiology of *M. leprae* due to their lack of highly polymorphic loci.

The present invention is directed to overcoming these and other deficiencies in the art.

SUMMARY OF THE INVENTION

The present invention relates to an isolated heat shock protein having an amino acid sequence at least 96 percent similar to the amino acid sequence of SEQ ID NOS: 1, 3, 5, 7, 9, 11, 13, and 15.

Another aspect of the present invention relates to a vaccine, and a method of vaccinating against onset of disease in subjects infected by *M. leprae* using an isolated heat shock protein according to the present invention in combination with a pharmaceutically-acceptable carrier.

The present invention also relates to a method of treating a subject with an atopic condition which involves administering an effective amount of an isolated heat shock protein according to the present invention under conditions effective to treat the subject against the onset of the atopic condition.

A further aspect of the present invention relates to a pharmaceutical composition composed of an adjuvant including an isolated heat shock protein according to the present invention and an antigen.

The present invention also relates to a method of inducing or enhancing an immune response against an antigen in a subject by administering an effective amount of a pharmaceutical composition comprising an adjuvant including an isolated heat shock protein and an antigen under conditions effective to induce or enhance an immune response against an antigen in the subject.

The present invention also relates to an isolated polynucleotide encoding a heat shock protein having an amino acid sequence at least 96 percent similar to the amino acid sequence of SEQ ID NOS: 1, 3, 5, 7, 9, 11, 13, and 15.

The present invention is also directed to a fusion protein composed of a heat shock protein having an amino acid sequence at least 96 percent similar to the amino acid sequence of SEQ ID NOS: 1, 3, 5, 7, 9, 11, 13, and 15 and an antigen, as well as a polynucleotide encoding the fusion protein.

The present invention also relates to a method of inducing or enhancing an immune response against an antigen in a subject by administering to the subject the fusion protein under conditions effective to induce or enhance the immune response against the antigen in the subject.

The present invention is further directed to an antibody raised against a heat shock protein having an amino acid sequence at least 96 percent similar to the amino acid sequence of SEQ ID NOS: 1, 3, 5, 7, 9, 11, 13, and 15.

Another aspect of the present invention relates to a method of treating a subject infected by *M. leprae* which involves administering an effective amount of the antibody raised against a heat shock protein according to the present invention, under conditions effective to treat the subject against *M. leprae* infection.

A further aspect of the present invention relates to a method for detection of *M. leprae* in a sample of tissue or body fluids which involves providing an antibody raised against a heat shock protein according to the present invention, contacting a sample with the antibody, and detecting any reaction which indicates that *M. leprae* is present in the sample.

Another aspect of the present invention relates to a method for detecting *M. leprae* in sample of tissue or body fluids by providing the isolated polynucleotide encoding an amino acid sequence at least 96 percent similar to the amino acid sequence of SEQ ID NOS: 1, 3, 5, 7, 9, 11, 13, and 15 as a probe in a nucleic acid hybridization assay, contacting the sample with the probe and detecting any reaction which indicates that *M. leprae* is present in the sample.

The present invention also relates to a method for detecting *M. leprae* in sample of tissue or body fluids by providing the isolated polynucleotide encoding an amino acid sequence at least 96 percent similar to the amino acid sequence of SEQ ID NOS: 1, 3, 5, 7, 9, 11, 13, and 15 as a probe in a PCR detection assay, contacting the sample with the probe, and detecting any reaction which indicates that *M. leprae* is present in the sample.

The present invention also relates to a method for detecting *M. leprae* in sample of tissue or body fluids by providing an isolated heat shock protein having an amino acid sequence at least 96 percent similar to the amino acid sequence of SEQ ID NOS: 1, 3, 5, 7, 9, 11, 13, or 15 as an antigen, contacting the sample with the antigen, and detecting any reaction with the antigen which indicates that *M. leprae* is present in the sample.

BRIEF DESCRIPTION OF THE DRAWINGS

FIGS. 1A-G show the % amino acid variation of SEQ ID NOS: 1, 3, 5, 7, 9, 11, 13, and 15 compared with the published amino acid sequence for Heat shock protein 65 ("Hsp65") in *Mycobacterium leprae*; SEQ ID NO. 17 (top).

FIGS. 2A-E show the % nucleotide variation of SEQ ID NOS: 2, 4, 6, 8, 10, 12, 14, and 16 compared with the published nucleotide sequence for Hsp65 in *Mycobacterium leprae*; SEQ ID NO. 18 (top).

DETAILED DESCRIPTION OF THE INVENTION

Figure 3:
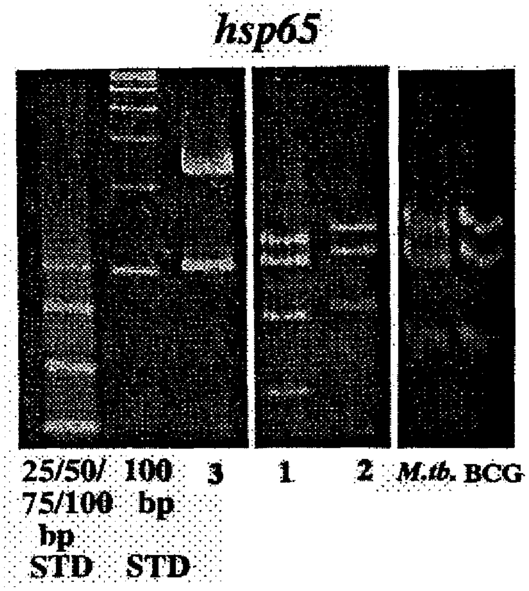
FIG. 3 shows the polyacrylamide gel electrophoresis (PAGE) of HaeIII digested PCR amplicons for Heat Shock Protein 65 (Hsp65). PAGE of HaeIII digested PCR amplicons from extracted DNA from skin lesions from a leprosy patient is shown. Lanes numbered 1-3 are from leprosy patients. *M. tb*. indicates the RFLP patterns for *Mycobacterium tuberculosis*. BCG indicates the RFLP patterns for Bovine cytomegalovirus.

One aspect of the present invention relates to isolated heat shock proteins of *Mycobacterium leprae*.

The first protein includes the amino acid sequence of SEQ ID NO:1 as follows:

```
Glu Lys Ile Gly Ala Glu Leu Val Lys Glu Val Ala Lys Lys Thr Asp
 1               5                  10                  15

Asp Val Ala Gly Asp Gly Thr Thr Thr Ala Thr Val Leu Ala Gln Ala
            20                  25                  30

Leu Val Lys Glu Gly Leu Arg Asn Val Ala Ala Gly Ala Asn Pro Leu
        35                  40                  45

Gly Leu Lys Arg Gly Ile Glu Lys Ala Val Asp Lys Ile Thr Gln Thr
    50                  55                  60

Leu Leu Asp Ser Ala Lys Asp Val Glu Thr Lys Glu Gln Ile Ala Ala
65                  70                  75                  80

Thr Ala Ser Ile Ser Ala Gly Asp Gln Ser Ile Gly Asp Leu Ile Ala
                85                  90                  95

Glu Ala Lys Asp Lys Val Gly Asn Glu Gly Val Ile Thr Val Glu Glu
            100                 105                 110

Ser
```

This protein is encoded by a polynucleotide molecule having a nucleotide sequence of SEQ ID NO:2 as follows:

```
gagaagatcg gcgccgagct ggtcaaggaa gtcgccaaga agaccgacga cgtcgccggt    60

gacggcacca cgacggccac cgtgctggcc caggccctgg tcaaagaggg tctgcgtaac   120

gttgctgcgg gcgccaaccc actgggtctg aagcgcggca tcgagaaggc cgtcgataag   180

atcacccaga cgctgctgga ctcggccaag gacgtcgaga ccaaggagca gatcgcagcc   240

accgctagca tttctgccgg tgaccagtcg atcggcgacc tgatcgccga agcgaaggac   300

aaggtcggca acgagggcgt catcaccgtc gaggagtcc                          339
```

The next protein includes the amino acid sequence of SEQ ID NO:3 as follows:

```
Glu Lys Ile Gly Ala Glu Leu Val Lys Glu Val Ala Lys Lys Thr Asp
 1               5                  10                  15

Asp Val Ala Gly Asp Gly Thr Thr Thr Ala Thr Val Leu Ala Gln Ala
            20                  25                  30

Leu Val Arg Glu Gly Leu Arg Asn Val Ala Ala Gly Ala Asn Pro Leu
        35                  40                  45

Gly Leu Lys Arg Gly Ile Glu Lys Ala Val Gly Lys Ile Thr Glu Val
    50                  55                  60

Leu Leu Ser Ser Ala Lys Asp Val Glu Thr Lys Glu Gln Ile Ala Ala
65                  70                  75                  80
```

-continued

```
Thr Ala Gly Ile Ser Ala Gly Asp Gln Ser Ile Gly Asp Leu Ile Ala
                85                  90                  95

Val Ala Met Asp Lys Val Gly Asn Glu Gly Ile Ile Thr Val Glu Glu
            100                 105                 110

Ser
```

This protein is encoded by a polynucleotide molecule having an amino acid sequence of SEQ ID NO:4 as follows:

```
gagacgatcg gcgccgagct ggtcaaggaa gtcgccaaga agaccgacga cgtcgccggt   60

gacggcacga cgacggccac ggtgctcgcc caggcgttgg tccgcgaggg cctgcgcaac  120

gtcgcggctg gcgccaaccc gctgggtctc aagcgcggca tcgagaaggc cgttggaaaa  180

atcacggaag ttctcccgtc gtcggccaag gacgtcgaga ccaaggagca gatcgctgcc  240

accgctggca tttctgccgg tgaCC&gtcg atcggcgacc tgatcgccgt agcgatggac  300

aaggtcggca acgagggcat catcaccgtc gaggagtcc                         339
```

The next protein includes the amino acid sequence of SEQ ID NO:5 as follows:

```
Glu Lys Ile Gly Ala Glu Leu Val Lys Glu Val Ala Lys Lys Thr Asp
  1               5                  10                  15

Asp Val Ala Gly Asp Gly Thr Thr Thr Ala Thr Val Leu Ala Glu Ala
            20                  25                  30

Leu Val Lys Glu Gly Leu Arg Asn Val Ala Ala Gly Ala Asn Pro Leu
        35                  40                  45

Gly Leu Lys Arg Gly Ile Glu Lys Ala Val Asp Lys Ile Thr Gln Thr
    50                  55                  60

Leu Leu Asp Ser Ala Lys Asp Val Gln Thr Lys Glu Gln Ile Ala Ala
 65                  70                  75                  80

Thr Ala Ala Ile Ser Ala Gly Asp Gln Ser Ile Gly Asp Leu Ile Ala
                85                  90                  95

Glu Ala Met Asp Lys Val Gly Asn Glu Gly Val Ile Thr Val Glu Glu
            100                 105                 110

Ser
```

This protein is encoded by a polynucleotide molecule having an amino acid sequence of SEQ ID NO:6 as follows:

```
gagaagatcg gcgccgagct ggtcaaggaa gtcgccaaga agaccgacga cgtcgccggt   60

gacggcacca cgacggccac cgtgctggcc caggccctgg ttaaagaggg tctgcgtaac  120

gttgctgcgg gcgccaaccc gctgggtctg aagcgcggca tcgagaaggc cgtcgataag  180

atcacacaga cgctgctgga ctcggccaag gacgtcgaga ccaaggagca gatcgctgcc  240

accgcggcca tctccgcggg cgaccagtct atcggcgacc tgatcgccga ggcgatggac  300

aaggtcggca acgagggcgt catcaccgtc gaggagtcc                         339
```

The next protein includes the amino acid sequence of SEQ ID NO:7 as follows:

```
Glu Lys Ile Gly Ala Glu Leu Val Lys Glu Val Ala Lys Lys Thr Asp
  1               5                  10                  15

Asp Val Ala Gly Asp Gly Thr Thr Thr Ala Thr Val Leu Ala Gln Ala
             20                  25                  30

Leu Val Lys Glu Gly Leu Arg Asn Val Ala Ala Gly Ala Asn Pro Leu
         35                  40                  45

Gly Leu Lys Arg Gly Ile Glu Lys Ala Val Asp Lys Ile Thr Gln Thr
     50                  55                  60

Leu Leu Asp Ser Ala Glu Asp Val Glu Thr Lys Glu Gln Ile Ala Ala
 65                  70                  75                  80

Thr Ala Gly Ile Pro Ala Gly Asp Gln Ser Ile Gly Asp Leu Ile Ala
                 85                  90                  95

Glu Ala Met Asp Lys Val Gly Asn Gly Ala Ser Ser Pro Ser Arg Ser
            100                 105                 110
```

This protein is encoded by a polynucleotide molecule having an amino acid sequence of SEQ ID NO:8 as follows:

```
gagaagatcg gcgccgagct ggtcaaggaa gtcgccaaga agacogacga cgtcgccggt   60

gacggcacga cgacggccac ggttctggcc caggccttgg tccgcgaggg cctgcgtaac  120

gtcgccgccg gcgccaaccc gctgggtctg aagcgcggca tcgagaaggc cgtcgataag  180

accacccaga cgctgctgga ctcggccgag gacgccgaga ccaaggagca gatcgctgcc  240

accgctggca tccctgccgg tgaccagtcg atcggcgacc tgatcgccga agcgatggac  33a

aaggtcggca acggggcgtc atcaccgccg aggagtcc                           338
```

The next protein includes the amino acid sequence of SEQ ID NO:9 as follows:

```
Glu Lys Ile Gly Ala Glu Leu Val Lys Glu Val Ala Lys Lys Thr Asp
  1               5                  10                  15

Asp Val Ala Gly Asp Gly Thr Thr Thr Ala Thr Val Leu Ala Gln Ala
             20                  25                  30

Leu Val Lys Glu Gly Leu Arg Arg Val Ala Ala Gly Ala Asn Pro Leu
         35                  40                  45

Gly Leu Lys Arg Gly Ile Glu Lys Ala Val Asp Lys Ile Thr Gln Thr
     50                  55                  60

Leu Leu Asp Pro Ala Lys Asp Val Glu Thr Lys Glu Gln Ile Ala Ala
 65                  70                  75                  80

Thr Ala Gly Thr Ser Ala Gly Asp Gln Ser Ile Gly Asp Pro Ile Ala
                 85                  90                  95

Glu Ala Met Asp Gly Val Gly Asn Glu Gly Val Ile Thr Val Glu Glu
            100                 105                 110

Ser
```

This protein is encoded by a polynucleotide molecule having an amino acid sequence of SEQ ID NO:10 as follows:

```
gagaagatcg gcgccgagct ggtcaaggaa gtcgccaaga agaccgacga cgtcgccggt   60

gacggcacca cggcggccac cgtgctggcc caggccctgg tcaaagaggg tctgcgtaac  120

gttgctgcgg gcgccaaccc gctgggtctg aagcgcggca tcgagaaggc cgtcgataag  180
```

-continued

```
accacccaga cgctgctgga cccggccaag gacgtcgaga ccaaggagca gatcgctgcc  240

accgctggca catcagccgg tgaccagtcg atcggcgacc cgatcgccga agcgatggac  300

gaggtcggca acgagggcgt catcaccgtc gaggagtcc                         339
```

The next protein includes the amino acid sequence of SEQ ID NO:11 as follows:

```
Glu Lys Ile Gly Ala Glu Leu Val Lys Glu Val Ala Lys Lys Thr Asp
  1               5                  10                  15

Glu Val Ala Cys Asp Gly Thr Thr Thr Ala Thr Val Leu Ala Gln Ala
             20                  25                  30

Leu Val Arg Glu Gly Leu Arg Asn Val Ala Ala Gly Ala Asp Pro Leu
         35                  40                  45

Ser Leu Lys Arg Gly Ile Glu Lys Ala Val Ala Ala Val Thr Glu Gln
     50                  55                  60

Leu Leu Ala Ser Ala Lys Glu Val Glu Thr Lys Glu Ala Ile Ala Ala
 65                  70                  75                  80

Thr Ala Ser Ile Ser Ala Ala Asp Thr Gln Ile Gly Ala Leu Ile Ala
                 85                  90                  95

Glu Ala Leu Asp Lys Val Gly Lys Glu Gly Val Ile Thr Val Glu Glu
            100                 105                 110

Ser
```

This protein is encoded by a polynucleotide molecule having an amino acid sequence of SEQ ID NO:12 as follows:

```
gagaagatcg gcgccgagct ggtcaaggaa gtcgccaaga agactgacga agtcgcctgc   60

gacggtacca ccaccgctac cgttctggcc caggccttgg ttcgcgaagg cttgcgcaac  120

gtcgcagccg gcgctgatcc gctgagcctc aagcgcggca tcgagaaggc tgtcgccgcg  180

gtgaccgagc agctgctggc ttccgccaag gaagtcgaga ccaaagaaga gatcgcggcc  240

actgcttcga tctccgccgc ggacacccag atcggcgcgt tgatcgccga agccctggac  300

aaggtcggca aagaaggcgt catcacggtc gaagagtcc                         339
```

The next protein includes the amino acid sequence of SEQ ID NO:13 as follows:

```
Glu Lys Ile Gly Ala Glu Leu Val Lys Glu Ala Ala Lys Lys Thr Asp
  1               5                  10                  15

Glu Val Ala Gly Asp Gly Thr Thr Thr Ala Thr Val Leu Ala Gln Ala
             20                  25                  30

Leu Val Arg Glu Glu Leu Arg Asn Val Ala Ala Gly Ala Asp Pro Leu
         35                  40                  45

Ser Leu Lys Arg Gly Ile Glu Lys Ala Val Ala Ala Val Thr Glu Gln
     50                  55                  60

Leu Leu Ala Ser Ala Lys Glu Val Glu Thr
 65                  70
```

This protein is encoded by a polynucleotide molecule having an amino acid sequence of SEQ ID NO:14 as follows:

```
gagaagatcg gcgccgagct ggtcaaggaa gccgccaaga agactgacga agtcgccggc   60

gacggtacca ccaccgctac cgttctggcc caggccttgg ttcgcgaagg cttgcgcaac  120
```

-continued

```
gtcgcagccg gcgctgatcc gctgagcctc aagcgcggca tcgagaaggc tgtcgccgcg  180

gcgaccgagc agctgctggc ttccgccaag gaagtcgaga cctaagaaga gatcgcggcc  240

actgcttcga tctccgccgc ggacacccag atcggcgcgt tgatcgccga agccctggac  330

aaggtcggca aagaaggcgt catcacggtc gaagagtcc                         339
```

The next protein includes the amino acid sequence of SEQ ID NO:15 as follows:

```
Glu Lys Ile Gly Ala Glu Leu Val Lys Glu Val Ala Lys Lys Thr Asp
  1               5                  10                  15

Glu Val Ala Gly Asp Gly Thr Thr Thr Ala Thr Val Leu Ala Gln Ala
            20                  25                  30

Leu Asp Arg Glu Gly Leu Arg Asn Val Ala Ala Gly Ala Asp Pro Leu
        35                  40                  45

Ser Leu Lys Arg Gly Ile Glu Lys Ala Val Ala Ala Val Thr Glu Gln
    50                  55                  60

Leu Leu Ala Ser Ala Lys Glu Val Glu Thr Lys Glu Glu Ile Ala Ala
 65                  70                  75                  80

Thr Ala Ser Ile Ser Ala Ala Asp Thr Gln Ile Gly Ala Leu Ile Ala
                 85                  90                  95

Glu Ala Leu Asp
            100
```

This protein is encoded by a polynucleotide molecule having an amino acid sequence of SEQ ID NO:16 as follows:

```
gaggagatcg gcgccgagct ggtcaaggaa gtcgccaaga agactgacga agtcgccggc   60

gacggtacca ccaccgctac cgttctggcc caggccttgg atcgcgaagg cttgcgcaac  120

gtcgcagccg gcgctgatcc gctgagcctc aagcgcggca tcgagaaggc tgtcgccgcg  180

gtgaccgagc agctgctggc ttccgccaag gaagtcgaga ccaaagaaga gatcgcggcc  240

actgcttcga tctccgccgC ggacacccag atcggcgcgt tgatcgccga agccctggac  330

taggtcggca aagaaggcgt catcacggtc gaagagtcc                         339
```

FIGS. 1A-G show an alignment of the proteins having the amino acid sequence of SEQ ID NOS: 1, 3, 5, 7, 9, 11, 13, and 15 against the publicly available amino acid sequence listed at genolist.pasteur.fr/Leproma/. FIGS. 2A-E show an alignment of the polynucleotides having the nucleotide sequences of SEQ ID NOS: 2, 4, 6, 8, 10, 12, 14, and 16 against the publicly available nucleotide sequence listed at id.

Another aspect of the present invention relates to an isolated polynucleotide encoding a heat shock protein where the heat shock protein has an amino acid sequence at least 96 percent, at least 98 percent, and 100 percent similar to the amino acid sequence of SEQ ID NOS: 1, 3, 5, 7, 9, 11, 13, and 15. The present invention also relates to an isolated polynucleotide encoding a heat shock protein having a nucleotide sequence at least 85 percent, at least 90 percent, at least 95 percent, at least 98 percent, and 100 percent similar to the nucleotide sequence of SEQ ID NOS: 2, 4, 6, 8, 10, 12, 14, and 16.

The determination of percent identity, i.e. sequence similarity, between two amino acid sequences or two nucleotide sequences can be accomplished using a mathematical algorithm. A preferred, non-limiting example of a mathematical algorithm utilized for the comparison of two sequences is the algorithm of Karlin et al., "Methods for Assessing the Statistical Significance of Molecular Sequence Features by Using General Scoring Schemes", *Proc. Natl. Acad. Sci.* 87:2264-2268 (1990), modified as in Karlin et al., "Applications and Statistics for Multiple High-scoring Segments in Molecular Sequences", *Proc. Natl. Acad. Sci.* 90:5873-5877 (1993). Another non-limiting example of a mathematical algorithm utilized for the comparison of sequences is the algorithm of Myers et al., CABIOS (1989). Such an algorithm can be incorporated into the ALIGN program (version 2.0) which is part of the CGC sequence alignment software package. Additional algorithms for sequence analysis are known in the art and include ADVANCE and ADAM as described in Torellis et al. "ADVANCE and ADAM: Two Algorithms for the Analysis of Global Similarity Between Homologous Informational Sequences", *Comput. Appl. Biosci.* 10:3-5 (1994); and FASTA described in Pearson et al., "Improved Tools for Biological Sequence Comparison", *Proc. Natl. Acad. Sci.* 85:2444-8 (1988).

Fragments of the above proteins are encompassed by the present invention.

The proteins of the present invention are preferably produced in purified form by conventional techniques. For example, to isolate the proteins, a protocol involving a host cell such as *Escherchia coil* may be used, in which the *E. coli* host cell carrying a recombinant plasmid is propagated, homogenized, and the homogenate is centrifuged to remove bacterial debris. The supernatant is then subjected to sequential ammonium sulfate precipitation. The fraction containing the proteins of the present invention can be subjected to gel filtration in an appropriately sized dextran or polyacrylamide column to separate the proteins or polypeptides. If necessary, the protein fraction may be further purified by HPLC.

Fragments of the proteins of the present invention can be produced by digestion of a full-length protein with proteolytic enzymes like chymotrypsin or *Staphylococcus* proteinase A, or trypsin. Different proteolytic enzymes are likely to cleave the proteins of the present invention at different sites based on the amino acid sequence of the proteins.

In another approach, based on knowledge of the primary structure of the protein, fragments of the genes encoding the proteins of the present invention may be synthesized by using a PCR technique together with specific sets of primers chosen to represent particular portions of the protein of interest. These then would be cloned into an appropriate vector for expression of a truncated peptide or protein.

Chemical synthesis can also be used to make suitable fragments. Such a synthesis is carried out using known amino acid sequences for the protein being produced. Alternatively, subjecting a full length protein of the present invention to high temperatures and pressures will produce fragments. These fragments can then be separated by conventional procedures (e.g., chromatography, SDS-PAGE).

Variants may also (or alternatively) be made, for example, by the deletion or addition of amino acids that have minimal influence on the properties, secondary structure and hydropathic nature of the protein. For example, a protein may be conjugated to a signal (or leader) sequence at the N-terminal end of the protein which co-translationally or post-translationally directs transfer of the protein. The protein may also be conjugated to a linker or other sequence for ease of synthesis, purification, or identification of the protein.

The protein of the present invention is preferably produced in purified form (preferably at least about 80%, more preferably 90%, pure) by conventional techniques. Typically, the protein of the present invention is secreted into the growth medium of *Helicobacter* cells or host cells which express a functional type III secretion system capable of secreting the protein of the present invention. Alternatively, the protein of the present invention is produced but not secreted into growth medium of recombinant host cells (e.g., *Escherichia coli*). In such cases, to isolate the protein, the host cell (e.g., *E. coli*) carrying a recombinant plasmid may be propagated, lysed by sonication, heat, differential pressure, or chemical treatment, and the homogenate is centrifuged to remove bacterial debris. The supernatant is then subjected to sequential ammonium sulfate precipitation. The fraction containing the polypeptide or protein of the present invention is subjected to gel filtration in an appropriately sized dextran or polyacrylamide column to separate the proteins. If necessary, the protein fraction may be further purified by HPLC.

Another aspect of the present invention relates to an expression system containing a polynucleotide encoding a heat shock protein according to the present invention.

The polynucleotides of the present invention may be inserted into any of the many available expression vectors using reagents that are well known in the art. In preparing a DNA vector for expression, the various DNA sequences may normally be inserted or substituted into a bacterial plasmid. Any convenient plasmid may be employed, which will be characterized by having a bacterial replication system, a marker which allows for selection in a bacterium, and generally one or more unique, conveniently located restriction sites. The selection of a vector will depend on the preferred transformation technique and target host for transformation.

Suitable vectors for practicing the present invention include, but are not limited to, the following viral vectors such as lambda vector system gt11, gtWES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK+/− or KS+/− (see "Stratagene Cloning Systems" Catalog (1993)), pQE, pIH821, pGEX, pET series (Studier et al, "*Use of T7 RNA Polymerase to Direct Expression of Cloned Genes*," Methods in Enzymology 185:60-89 (1990) which is hereby incorporated by reference in its entirety), and any derivatives thereof. Any appropriate vectors now known or later described for genetic transformation are suitable for use with the present invention. Recombinant molecules can be introduced into cells via transformation, particularly transduction, conjugation, mobilization, or electroporation. The DNA sequences are cloned into the vector using standard cloning procedures in the art, as described by Maniatis et al., Molecular Cloning: A Laboratory Manual, Cold Springs Harbor, N.Y.: Cold Springs Laboratory, (1982), which is hereby incorporated by reference in its entirety.

U.S. Pat. No. 4,237,224 issued to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

A further aspect of the present invention relates to a host cell containing a polynucleotide encoding a heat shock protein according to the present invention.

A variety of host-vector systems may be utilized to express the protein-encoding sequence(s) of the present invention. Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used.

The protein according to the present invention can be incorporated into an appropriate vector in the sense direction, such that the open reading frame is properly oriented for the expression of the encoded protein under control of a promoter of choice. This involves the inclusion of the appropriate regulatory elements into the DNA-vector construct. These include non-translated regions of the vector, useful promoters, and 5' and 3' untranslated regions which interact with host cellular proteins to carry out transcription and translation. Such elements may vary in their strength and specificity. Depending on the vector system and host utilized, any number of suitable transcription and translation elements, including constitutive and inducible promoters, may be used.

A constitutive promoter is a promoter that directs expression of a gene throughout the development and life of an organism.

An inducible promoter is a promoter that is capable of directly or indirectly activating transcription of one or more DNA sequences or genes in response to an inducer. In the absence of an inducer, the DNA sequences or genes will not be transcribed.

The expression system of the present invention can also include an operable 3' regulatory region, selected from among those which are capable of providing correct transcription termination and polyadenylation of mRNA for expression in the host cell of choice, operably linked to a DNA molecule which encodes for a protein of choice.

The vector of choice, promoter, and an appropriate 3' regulatory region can be ligated together to produce the DNA construct of the present invention using well known molecular cloning techniques as described in Sambrook et al., Molecular Cloning: A Laboratory Manual, Second Edition, Cold Spring Harbor Press, NY (1989), and Ausubel, F. M. et al. Current Protocols in Molecular Biology, New York, N.Y.: John Wiley & Sons, (1989), which are hereby incorporated by reference in their entirety.

The efficiency of expression can be enhanced by the inclusion of appropriate transcription or translation enhancer elements (e.g., elements disclosed in Bittner et al., *Methods in Enzymol.* 153:516, 1987). Additionally, the gene sequence can be modified for optimal codon usage in the appropriate expression system, or alternatively, the expression host can be modified to express specific tRNA molecules to facilitate expression of the desired gene.

In addition, the recombinant expression vector can contain additional nucleotide sequences. For example, the recombinant expression vector may encode a selectable marker gene to identify host cells that have incorporated the vector. Moreover, to facilitate secretion of the protein from a host cell, in particular mammalian host cells, the recombinant expression vector can encode a signal sequence linked to the amino-terminus of the protein, such that upon expression, the protein is synthesized with the signal sequence fused to its amino terminus. This signal sequence directs the protein into the secretory pathway of the cell and is then usually cleaved, allowing for release of the protein without the signal sequence from the host cell. Use of a signal sequence to facilitate secretion of proteins or peptides from mammalian host cells is well known in the art.

Once an expression system containing a polynucleotide according to the present invention has been prepared, it is ready to be incorporated into a host cell. Basically, this method can be carried out by transforming a host cell with the expression system of the present invention under conditions effective to yield transcription of the DNA molecule in the host cell. Recombinant molecules can be introduced into cells via transformation, particularly transduction, conjugation, mobilization, or electroporation. The DNA sequences are cloned into the host cell using standard cloning procedures known in the art, as described by Sambrook et al., Molecular Cloning: A Laboratory Manual, Second Edition, Cold Springs Laboratory, Cold Springs Harbor, N.Y. (1989), which is hereby incorporated by reference in its entirety. Suitable host cells include, but are not limited to, bacteria, virus, yeast, mammalian cells, insect, plant, and the like.

Another aspect of the present invention relates to a method of treating a subject with an atopic condition which involves administering an effective amount of an isolated heat shock protein according to the present invention under conditions effective to treat the subject against the onset of an atopic condition. The atopic conditions which can be treated include hay fever, asthma, and eczema.

Compounds of the present invention, including isolated heat shock proteins and antibodies raised against these proteins, can be administered orally, parenterally, for example, subcutaneously, intravenously, intramuscularly, intraperitoneally, by intranasal instillation, or by application to mucous membranes, such as, that of the nose, throat, and bronchial tubes. They may be administered alone or with suitable pharmaceutical carriers, and can be in solid or liquid form such as, tablets, capsules, powders, solutions, suspensions, or emulsions.

The active compounds of the present invention may be orally administered, for example, with an inert diluent, or with an assimilable edible carrier, or they may be enclosed in hard or soft shell capsules, or they may be compressed into tablets, or they may be incorporated directly with the food of the diet. For oral therapeutic administration, these active compounds may be incorporated with excipients and used in the form of tablets, capsules, elixirs, suspensions, syrups, and the like. Such compositions and preparations should contain at least 0.1% of active compound. The percentage of the compound in these compositions may, of course, be varied and may conveniently be between about 2% to about 60% of the weight of the unit. The amount of active compound in such therapeutically useful compositions is such that a suitable dosage will be obtained. Preferred compositions according to the present invention are prepared so that an oral dosage unit contains between about 1 and 250 mg of active compound.

The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it may contain, in addition to materials of the above type, a liquid carrier, such as a fatty oil.

Various other materials may be present as coatings or to modify the physical form of the dosage unit. For instance, tablets may be coated with shellac, sugar, or both. A syrup may contain, in addition to active ingredient, sucrose as a sweetening agent, methyl and propylparabens as preservatives, a dye, and flavoring such as cherry or orange flavor.

These active compounds may also be administered parenterally. Solutions or suspensions of these active compounds can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The compounds of the present invention may also be administered directly to the airways in the form of an aerosol. For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

Another aspect of the present invention relates to a pharmaceutical composition made of an adjuvant, comprised of an isolated heat shock protein according to the present invention, and an antigen.

The primary purpose of the adjuvant is to enhance the immune response to a particular antigen of interest. In the context of antibody production for research purposes, adjuvants stimulate the rapid and sustained production of high titers of antibodies with high avidity. This permits ready recovery of antibody for further research in vitro. Adjuvants have the capability of influencing titer, response duration, isotype, avidity, and some properties of cell-mediated immunity. The use of adjuvants is required for many antigens which by themselves are weakly immunogenic.

Adjuvants may act through three basic mechanisms. The first is to enhance long term release of the antigen by functioning as a depot. Long term exposure to the antigen should increase the length of time the immune system is presented with the antigen for processing as well as the duration of the antibody response. The second is the interaction the adjuvant has with immune cells. Adjuvants may act as non-specific mediators of immune cell function by stimulating or modulating immune cells. Adjuvants may also enhance macrophage phagocytosis after binding the antigen as a particulate (a carrier/vehicle function).

Other factors which influence the inflammatory response include antigen preparation, antigen-adjuvant mixture, injection sites (number and location), volume injected per site and condition of the animal. Antigens should be as sterile as possible and free of chemical contaminants. Antigens should also not be extremely acidic or basic. Excessive quantities of antigen-adjuvant should not be injected per site in order to decrease local inflammatory response. Animals used for antibody production should be in overall good health and free of disease.

According to the present invention, the antigen in the pharmaceutical composition can be a papillomavirus antigen, herpes simplex virus antigen, hepatitis B virus antigen, hepatitis C virus antigen, cytomegalovirus antigen, Epstein-Barr virus antigen, influenza virus antigen, measles virus antigen, human immunodeficiency virus antigen, bacterial antigen, mycoplasm antigen, mycobacterial antigen, fungus antigen, protozoan antigen, or a tumor-associated antigen. When the antigen is a tumor-associated antigen, it can be selected from a MAGE1, MAGE2, MAGE3, BAGE, GAGE, PRAME, SSX-2, Tyrosinase, MART-1, NY-ESO-1, gp100, TRP-1, TRP-2, A2 melanotope, BCR/ABL, Proteinase-3/Myeloblastin, HER2neu, CEA, p1A, HK2, PAPA, PSA, PSCA, PSMA, pg75, MUM-1, MUC-1, E6, E7, GnT-V, Beta-catenin, CDK4, or P15 antigen.

A further aspect of the present invention relates to a method of inducing or enhancing an immune response against an antigen in a subject. This method involves administering an effective amount of the pharmaceutical composition, made of an adjuvant comprised of an isolated heat shock protein according to the present invention and an antigen, under conditions effective to induce or enhance an immune response against an antigen in the subject. In carrying out this aspect of the present invention, the pharmaceutical composition is formulated and administered in substantially the same way as noted above.

Another aspect of the present invention relates to a fusion protein made of a heat shock protein having an amino acid sequence at least 96 percent similar to the amino acid sequence of SEQ ID NOS: 1, 3, 5, 7, 9, 11, 13, and 15 and an antigen. In one embodiment the fusion protein contains a heat shock protein which has the identical amino acid sequence of SEQ ID NOS: 1, 3, 5, 7, 9, 11, 13, and 15.

The present invention provides for fusion proteins containing heat shock protein(s) ("Hsp") according to the present invention, and an antigen. As used herein, a "fusion protein" is a non-naturally occurring polypeptide containing at least two amino acid sequences which generally are from two different proteins. The amino acid sequence of the full length fusion protein is not identical to the amino acid sequence of a naturally occurring protein or a fragment thereof. An Hsp fusion protein contains an Hsp or a fragment thereof at least eight amino acids in length linked to a heterologous polypeptide. A "heterologous polypeptide" refers to a polypeptide that is fused to the Hsp or fragment thereof and consists of an antigen as disclosed herein. The heterologous polypeptide is preferably at least eight amino acids in length. In some embodiments, the heterologous polypeptide is at least 10, 20, 50, 100, 150, 180, 200, or 300 amino acids in length. The heterologous polypeptide generally is not part or all of a naturally occurring Hsp. However, the fusion protein can also be a fusion between a first Hsp and a second, different, lisp, or between all or portion of an Hsp fused to all or a portion of the same Hsp (as long as the resultant fusion is not identical to a naturally occurring protein). The Hsp polypeptide can be attached to the N-terminus or C-terminus of the heterologous polypeptide. Preferably the fusion protein is a purified protein. See U.S. Pat. No. 6,657,055 to Siegel et al., which is hereby incorporated by reference in its entirety.

The preferred Hsp fusion protein has one Hsp protein linked to one heterologous polypeptide, i.e. antigen polypeptide, but other conformations are within the invention. For example, the fusion protein can contain at least two different heterologous polypeptides, e.g., two or more fragments of a single antigenic protein representing different epitopes or fragments of two or more different antigenic proteins derived from the same or different tumors or pathogens, and/or at least two different Hsp proteins.

The Hsp and heterologous polypeptide can be directly fused without a linker sequence. In preferred embodiments, the C-terminus of the Hsp can be directly fused to the N-terminus of the heterologous polypeptide or the C-terminus of the heterologous polypeptide can be directly fused to the N-terminus of the Hsp.

Alternatively, Hsp and heterologous polypeptides can be linked to each other via a peptide linker sequence. Preferred linker sequences (1) should adopt a flexible extended conformation, (2) should not exhibit a propensity for developing an ordered secondary structure which could interact with the functional Hsp and heterologous polypeptide domains, and (3) should have minimal hydrophobic or charged character, which could promote interaction with the functional protein domains. Typical surface amino acids in flexible protein regions include Gly, Asn, and Ser. Permutations of amino acid sequences containing Gly, Asn, and Ser would be expected to satisfy the above criteria for a linker sequence. Other neutral or near-neutral amino acids, such as Thr and Ala, can also be used in the linker sequence. Any other amino acid can also be used in the linker. A linker sequence length of fewer than 20 amino acids can be used to provide a suitable separation of functional protein domains, although longer linker sequences may also be used.

The Hsp fusion protein may be further fused to another amino acid sequence that facilitates the purification of the fusion protein. One useful fusion protein is a GST fusion protein in which the Hsp-heterologous polypeptide sequences are fused to the C-terminus or N-terminus of the GST sequence. Another useful fusion protein is a poly-histidine (His) fusion protein in which the Hsp-heterologous polypeptide sequences are fused to either the C-terminus or N-terminus of the poly-histidine sequence, e.g. Hisx6. In another embodiment, the fusion protein contains the chitin-binding region of intein, thereby permitting the purification of the fusion protein by chitin beads (Hoang et al., Construction and Use of Low-copy Number T7 Expression Vectors for Purification of Problem Proteins: Purification of *Mycobacterium tuberculosis* RhII and *Pseudomonas aeruginosa* Last and RhII Proteins, and Functional Analysis of Purified RhII Gene 1999 237:361-71 (1999), which is hereby incorporated by reference in its entirety). In another embodiment, the fusion protein contains a signal sequence from another protein. In certain host cells (e.g., mammalian host cells), expression and/or secretion of the Hsp fusion protein can be increased through use of a heterologous signal sequence. For example, the gp67 secretory sequence of the baculovirus envelope protein can be used as a heterologous signal sequence (*Current Protocols in Molecular Biology*, Ausubel et al., eds., John Wiley & Sons (1992), which is hereby incorporated by reference in its entirety). Other examples of eukaryotic signal sequences include the secretory sequences of melittin and human placental alkaline phosphatase (Stratagene; La Jolla, Calif.). Prokaryotic signal sequences useful for increasing secretion by a prokaryotic host cell include the phoA secretory signal (Molecular Cloning, Sambrook et al., second edition, Cold Spring Harbor Laboratory Press, 1989) and the protein A secretory signal (Pharmacia Biotech; Piscataway, N.J.).

Fusion proteins of the present invention, e.g., a fusion protein of Hsp65 and one of the listed antigens according to the present invention, can be produced by standard recombinant techniques, as described above. For example, DNA fragments coding for the different polypeptide sequences are ligated together, in any order, in-frame in accordance with conventional techniques. Such techniques can include employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. Correct linkage of the two nucleic acids requires that the product of the linkage encode a chimeric protein consisting of a Hsp moiety and a heterologous polypeptide moiety. In another embodiment, the fusion gene can be synthesized by conventional techniques, including automated DNA synthesizers. Alternatively, PCR amplification of gene fragments can be carried out using anchor primers which give rise to complementary overhangs between two consecutive gene fragments, which are subsequently annealed and reamplified to generate a chimeric gene sequence (see, e.g., *Current Protocols in Molecular Biology*, Ausubel et al. eds., John Wiley & Sons, 1992).

The heterologous polypeptides can contain any amino acid sequence useful for stimulating an immune response, in vitro and/or in vivo. Preferably, the heterologous polypeptide contains an MHC-binding epitope, e.g., an MHC class I or MHC class II binding epitope. The heterologous polypeptide can contain sequences found in a protein produced by a human pathogen, e.g., viruses, bacteria, *mycoplasm*, mycobateria, fungi, protozoa, and other parasites, or sequences found in the protein of a tumor associated antigen (TAA). Examples of viruses include human papilloma virus (HPV), herpes simplex virus (HSV), hepatitis B virus (HBV), hepatitis C virus (HCV), cytomegalovirus (CMV), Epstein-Barr virus (EBV), influenza virus, measles virus, and human immunodeficiency virus (HIV). Examples of tumor associated antigens include MAGE1, MAGE2, MAGES, BAGE, GAGE, PRAME, SSX-2, Tyrosinase, MART-1, NY-ESO-1, gp100, TRP-1, TRP-2, A2 melanotope, BCR/ABL, Proeinase-3/Myeloblastin, HER2/neu, CEA, P1A, HK2, PAPA, PSA, PSCA, PSMA, pg75, MUM-1, MUC-1, E6, E7, GnT-V, Beta-catenin, CDK4 and P15.

It would be useful if the fusion proteins were soluble under normal physiological conditions. Also within the scope of the present invention are methods of using fusion proteins (or other configurations of proteins, including covalent and non-covalent complexes and mixtures) in which the stress protein (or an immunostimulatory fragment thereof) and an antigen are fused to (or otherwise associated with) an unrelated third protein or polypeptide to create at least a tripartite protein or mixture of proteins. The third protein may facilitate purification, detection, or solubilization of the fusion or other complex, or it may provide some other function. For example, the expression vector pUR278 (Ruther et al., “Easy Identification of cDNA Clones,” *EMBO J.* 2:1791 (1983), which is hereby incorporated by reference in its entirety) can be used to create lacZ fusion proteins. The pGEX vectors can be used to express foreign polypeptides as fusion proteins containing glutathione S-transferase (GST). In general, such fusion proteins are soluble and can be easily purified from lysed cells by adsorption to glutathione-agarose beads, followed by elution in the presence of free glutathione. The pGEX vectors are designed to include thrombin or factor Xa protease cleavage sites so that the cloned target gene product can be released from the GST moiety.

In addition to the recombinant techniques described above, a fusion protein of the invention can be formed by linking two polypeptides, e.g., a Hsp and a heterologous polypeptide, to form a conjugate. Methods of forming Hsp conjugates are described in WO 89/12455, WO 94/29459, WO 98/23735, and WO 99/07860, the contents of which are herein incorporated by reference in their entirety. As used herein, an Hsp “conjugate” comprises an lisp that has been covalently linked to a heterologous polypeptide via the action of a coupling agent. A conjugate thus comprises two separate molecules that have been coupled one to the other. The term “coupling agent,” as used herein, refers to a reagent capable of coupling one polypeptide to another polypeptide, e.g., a Hsp to a heterologous polypeptide. Any bond which is capable of linking the components such that the linkage is stable under physiological conditions for the time needed for the assay (e.g., at least 12 hours, preferably at least 72 hours) is suitable. The link between two components may be direct, e.g., where a Hsp is linked directly to a heterologous polypeptide, or indirect, e.g., where a Hsp is linked to an intermediate, e.g., a backbone, and that intermediate is also linked to the heterologous polypeptide. A coupling agent should function under conditions of temperature, pH, salt, solvent system, and other reactants that substantially retain the chemical stability of the Hsp, the backbone (if present), and the heterologous polypeptide.

In addition to conjugates of two polypeptides, e.g., a Hsp and a heterologous polypeptide, hybrid compounds can be constructed containing a non-peptide compound covalently linked to a polypeptide at least eight amino acids in length.

The polypeptide component of this hybrid compound can be any of the heterologous polypeptides described herein as a component of a Hsp fusion protein or conjugate. Examples of the non-peptide component of this hybrid compound include polynucleotides, polynucleotide analogs, nucleotides, nucleotide analogs, organic or inorganic compounds having a molecular weight less than about 5,000 grams per mole, preferably between about 1,500 and 100 grams per mole, and salts, esters, and other pharmaceutically acceptable forms of such non-peptide compounds.

Another aspect of the present invention relates to a method of inducing or enhancing an immune response against an antigen in a subject. The method involves administering to the subject a fusion protein according to the present invention under conditions effective to induce or enhance an immune response against the antigen in the subject. In carrying out this aspect of the present invention, the fusion protein is formulated and administered in substantially the same way as noted above.

Another aspect of the present invention relates to a pharmaceutical composition made of a fusion protein, and a pharmaceutically acceptable carrier or excipient as described herein according to the present invention.

A further aspect of the present invention relates to a method of inducing or enhancing an immune response against an antigen in a subject. The method involves administering to the subject a pharmaceutical composition made of a fusion protein according to the present invention, and a pharmaceutically acceptable carrier or excipient under conditions effective to induce or enhance the immune response against the antigen in the subject. In carrying out this aspect of the present invention, the pharmaceutical composition is formulated and administered in substantially the same way as noted above.

Another aspect of the present invention relates to a method for detection of *M. leprae* in a sample of tissue or body fluids. The method involves providing a polynucleotide encoding an isolated heat shock protein according to the present invention as a probe in a nucleic acid hybridization assay, contacting the sample with the probe, and detecting any reaction which indicates that *M. leprae* is present in the sample.

The polynucleotides may be used in any nucleic acid hybridization assay system known in the art, including, but not limited to, Southern blots (Southern, J. Mol. Biol. 98: 503-517 (1975) (which discloses hybridization in 2×SSC (i.e., 0.15M NaCl, 0.015 sodium citrate), 40% formamide at 40 degrees Celsius; Northern blots (Thomas et al., *Proc. Nat'l Acad. Sci. USA* 77:5201-05 (1980)); Colony blots (Grunstein et al. *Proc. Nat'l Acad. Sci. USA* 72:3961-65 (1975), which are hereby incorporated by reference in their entirety).

Another aspect of the present invention relates to a method for detection of *M. leprae* in a sample of tissue or body fluids. The method involves providing a polynucleotide according to the present invention as a probe in a PCR detection assay, contacting the sample with the probe, and detecting any reaction which indicates that *M. leprae* is present in the sample. See H. A. Erlich et al., "Recent Advances in the Polymerase Chain Reaction," *Science* 252:1643-51 (1991), which is hereby incorporated by reference in its entirety.

Another aspect of the present invention relates to a method for detection of *M. leprae* in a sample of tissue or body fluids. The method involves providing an isolated heat shock protein according to the present invention as an antigen, contacting the sample with the antigen, and detecting any reaction with the antigen which indicates that *M. leprae* is present in the sample.

Examples of suitable methods for detection of *M. leprae* include an enzyme-linked immunosorbent assay, a radioimmunoassay, a gel diffusion precipitan reaction assay, an immunodiffusion assay, an agglutination assay, a fluorescent immunoassay, a protein A immunoassay, or an immunoelectrophoresis assay. Such techniques can permit detection of *M. leprae* in a sample of the following tissue or body fluids: blood, spinal fluid, sputum, pleural fluids, urine, bronchial alveolor lavage, lymph nodes, bone marrow, or other biopsied materials.

The present invention is further directed to an antibody raised against a heat shock protein having an amino acid sequence at least 96 percent similar to the amino acid sequence of SEQ ID NOS: 1, 3, 5, 7, 9, 11, 13, and 15.

Isolated antibodies, or binding portions thereof, raised against an isolated heat shock protein of the present invention, can be used for detecting *M. leprae* or for passive immunization of subjects. The antibodies may be monoclonal or polyclonal.

Monoclonal antibody production may be effected by techniques which are well-known in the art. (See, e.g., Harlow and Lane, Antibodies: A Laboratory Manual, Cold Spring Harbor Laboratory Press, Cold Spring Harbor, N.Y. for descriptions of such methods). First, mammalian lymphocytes are immunized by in vivo immunization of an animal (e.g., a mouse) with a protein of interest, i.e. an *M. leprae* protein having SEQ ID NO: 1, 3, 5, 7, 9, 11, 13, or 15. Such immunizations are repeated as necessary at intervals of up to several weeks to obtain a sufficient titer of antibodies. Following the last antigen boost, the animals are sacrificed and spleen cells removed.

Next, the antibody-secreting lymphocytes are fused with (mouse) myeloma cells or transformed cells, which are capable of replicating indefinitely in cell culture, thereby producing an immortal, immunoglobulin-secreting cell line. The resulting fused cells, or hybridomas, are cultured, and the resulting colonies screened for the production of the desired monoclonal antibodies. Colonies producing such antibodies are cloned, and grown either in vivo or in vitro to produce large quantities of antibody. A description of the theoretical basis and practical methodology of fusing such cells is set forth in Kohler and Milstein, "Continuous Culture of Fused Cells Secreting Antibody of Predefined Specificity," *Nature,* 256:495-7 (1975), which is hereby incorporated by reference in its entirety.

Fusion with mammalian myeloma cells or other fusion partners capable of replicating indefinitely in cell culture is effected by standard and well-known techniques, for example, by using polyethylene glycol ("PEG") or other fusing agents (Milstein et al., "Derivation of Specific Antibody-Producing Tissue Culture and Tumor Lines by Cell Fusion," *Eur. Immunol.,* 6:511-19 (1976), which is hereby incorporated by reference in its entirety). This immortal cell line, which may be derived from cells of any mammalian species, including, but not limited to, mouse, rat, and human, is selected to be deficient in enzymes necessary for the utilization of certain nutrients, to be capable of rapid growth, and to have good fusion capability. Many such cell lines are known to those skilled in the art, and others are regularly described.

Procedures for raising polyclonal antibodies are also well known in the art. Typically, such antibodies can be raised by administering a protein, i.e., an *M. leprae* protein having SEQ ID NO: 1, 3, 5, 7, 9, 11, 13, or 15, subcutaneously to New Zealand white rabbits which have first been bled to obtain pre-immune serum. The antigens can be injected at a total volume of 100 μl per site at six different sites. Each injected material will contain synthetic surfactant adjuvant pluronic polyols, or pulverized acrylamide gel containing a protein according to the present invention after SDS-polyacrylamide gel electrophoresis. The rabbits are then bled two weeks after the first injection and periodically boosted with the same antigen three times every six weeks. A sample of serum is then collected 10 days after each boost. Polyclonal antibodies are then recovered from the serum by affinity chromatography using the corresponding antigen to capture the antibody. Ultimately, the rabbits are euthenized with pentobarbital 150 mg/Kg IV. This and other procedures for raising polyclonal antibodies are disclosed in E. Harlow, et. al., Editors, *Antibodies: a Laboratory Manual* (1988), which is hereby incorporated by reference in its entirety. However, it is not intended that the present invention be limited to any particular antibody preparation. Thus, antibodies useful in the present invention include, but are not limited to polyclonals, monoclonals, chimerics, single chains, Fab fragments, and Fab expression libraries.

The present invention also affords a method for detection of *M. leprae* in a sample of tissue or body fluids. This method involves providing an antibody, or binding portion thereof, against a protein of the present invention, contacting the sample with the antibody under conditions effective to allow formation of a complex of the antibody and an antigen recognized by the antibody, and detecting if any of the complex is present, thereby indicating the presence of *M. leprae* in the sample. As indicated above, antibodies suitable for use in accordance with the present invention include monoclonal or polyclonal antibodies. In addition, antibody fragments, half-antibodies, hybrid derivatives, probes, and other molecular constructs may be utilized. Also suitable are binding portions of such antibodies. Such binding portions include Fab fragments, $F(ab')_2$ fragments, and Fv fragments. These antibody fragments can be made by conventional procedures, such as proteolytic fragmentation procedures, as described in J. Goding, *Monoclonal Antibodies: Principles and Practice*, pp. 98-118 (N.Y. Academic Press 1983), which is hereby incorporated by reference in its entirety. Detecting may be carried out by any assay system capable of detecting a complex of the antibody, or binding portion thereof, and an antigen recognized by the antibody, including, but not limited to, those described supra. The antibody, or binding portion thereof, may also be labeled for use in a suitable assay system.

Another aspect of the present invention relates to a method of treating a subject infected by *M. leprae* which involves administering an effective amount of the antibody raised against a heat shock protein according to the present invention, under conditions effective to treat the subject against *M. leprae* infection.

Isolated antibodies raised against an isolated heat shock protein of the present invention can be used for passively immunizing subjects infected with *Mycobacterium leprae*. See U.S. Pat. No. 6,214,341 to Thomas et. al, which is hereby incorporated by reference in its entirety. Passive immunization of a subject can be achieved by injecting, for example, a subject with preformed antibodies raised against an antigen, e.g., an isolated heat shock protein of the present invention. The isolated antibodies can be combined with a pharmaceutically-acceptable carrier, as noted above, and then administered, in an effective amount, to a subject infected with *Mycobacterium leprae*. Suitable methods of administration are as described herein, supra.

EXAMPLES

The following examples are provided to illustrate embodiments of the present invention but are by no means intended to limit its scope.

Example 1

Study Population and DNA Extraction

Samples embedded in paraffin were scrapped from slides or used directly from paraffin sliced sections. Paraffin was removed by incubation for 5 minutes with 1 ml xylene, microfuged for 10 minutes at room temperature, washed with ethanol (2X-1 ml), spun at room temperature for 5 minutes in a microfuge and dried. DNA was re-suspended in 0.5 ml low-TE (1 mM Tris-0.2 mM EDTA, pH 7.5)-2% SDS-0.5 mg/ml-proteinase K and incubated at 50° C. for 1-2 days. Samples were extracted with phenol-chloroform/chloroform and precipitated with 0.4 M sodium chloride in two volumes of ethanol. Samples were re-digested with proteinase K; phenol extracted and ethanol precipitated as before. DNA was dried and re-suspended in 200 μl sterile water.

Example 2

PCR Amplification of folP, gyrA, gyrB and hsp65 Genes

PCR was performed using published primer sequences for the hsp65, folP, gyrA and gyrB genes (Table 1). Two volumes of DNA (2 and 20 μl) were used to ensure sufficient template. Specific sense and anti-sense primers (25-50 ng) and DNA were used with Tag polymerase (Promega, Madison, Wis.) (35-40 cycles for 1.0 minute at 94° C.-dissociation, 55°-61° C. annealing, extension for 1 minute at 72° C., with a 10 minute final cycle). For nested PCR, 3 μl of the first PCR amplicon was used and the annealing temperature was increased by 2° C. The PCR amplicons (20 μl) was electrophoresed in 2% agarose containing ethidium bromide (0.4 μg/mL) (Ausubel, "In: Current Protocols in Molecular Biology," Wiley and Sons, New York, (1992), which is hereby incorporated by reference in its entirety) and visualized under ultra violet light. For hsp65 RFLP, PCR amplicons were purified by phenol-chloroform extraction and ethanol precipitation before digestion with HaeIII and then electrophoresed in 10% PAGE in TBE (0.044 M Tris, 0.045 M boric acid, 1 mM EDTA) followed by staining with ethidium bromide post-electrophoresis (Shin et al., "Variable Numbers of TTC Repeats in *Mycobacterium leprae* DNA from Leprosy Patients and Use in Strain Differentiation," *J. Clinical Microbiology* 38:4535-4538 (2000), Chae et al., "Typing of Clinical Isolates of *Mycobacterium leprae* and Their Distribution in Korea," *Leprosy Review* 73:41-46 (2002), Young, D. "Prospects for Molecular Epidemiology of Leprosy," *Leprosy Review.* 74:11-17 (1993), Young et al., "Leprosy, Tuberculosis, and the New Genetics," *J. Bacteriology.* 175:1-6 (1993), Cole et al., "Repetitive Sequences in *Mycobacterium leprae* and Their Impact on Genome Plasticity," *Leprosy Review* 72:449-461 (2001), Matsuoka et al., "*Mycobacterium leprae* Typing by Genomic Diversity and Global Distribution of Genotypes," *International J. Leprosy* 68:121-128 (2000), which are hereby incorporated by reference in their entirety).

TABLE 1

| Primer Sequences | | Location | |
|---|---|---|---|
| hsp65 primers BX842573 Rv0440 186701-188323 | | | |
| tb11 | 5'-caccaacgatggtgtccatcgc-3' | 144-165 | SEQ ID NO: 19 |
| tb12 | 5'-cttgtcgaaccgcataccctc-3' | 575-596 | SEQ ID NO: 20 |
| nested tb-11A | 5'-aggagatcgagctggaggatccgta-3' | 168-192 | SEQ ID NO: 21 |
| tb-12B | 5'-gagctgcagcccaaaggtgttg-3' | 545-572 | SEQ ID NO: 22 |
| folP primers AL0234193 | | | |
| folP-outer-S | 5'-cccgtgcaacatcagcgcgcgtagtatcga-3' | 5060-5089 | SEQ ID NO: 23 |
| folP-outer-AS | 5'-actgacaattcgttctcagatggcggacgt-3' | 5271-5300 | SEQ ID NO: 24 |
| nested folP-S | 5'-tacttactgtaatcccctgtgctg-3 | 5090-5113 | SEQ ID NO: 25 |
| folP-AS | 5'-ttgatcctgacgatgctgtc-3' | 5247-5266 | SEQ ID NO: 26 |
| gyrA primers 768206 | | | |
| gyrA-outer-S | 5'-gtcgggtcttgtacgcgatgttagactccg-3' | 161-190 | SEQ ID NO: 27 |
| gyrA-outer-AS | 5'-caacctcaccaaggaatttcctgacacaCa-3' | 391-420 | SEQ ID NO: 28 |
| nested gyrA-S | 5'-cccggaccgtagccacgctaagtc-3' | 198-221 | SEQ ID NO: 29 |
| gyrA-AS | 5'-catcgctgccggtgggtcatta-3' | 363-384 | SEQ ID NO: 30 |
| gyrB primers 768206 | | | |
| gyB-outer-S | 5'-ttggtggacttcctggaaaaacttgccgatt-3' | 6541-6570 | SEQ ID NO: 31 |
| gyrB-outer-AS | 5'-cctggagatatcgaattcatcatggattcC-3 | 6771-6800 | SEQ ID NO: 32 |
| nested gyrB-S | 5'-actgatcctcgaagttctgaactg'3' | 6579-6603 | SEQ ID NO: 33 |
| gyrB-AS | 5'-caatgccgtaataattgcttgaa-3' | 6742-6764 | SEQ ID NO: 34 |

Example 3

Dideoxy Chain Termination DNA Sequencing

Sequencing was performed with the Thermo-Sequence Radio Labeled Terminator Cycle Sequencing Kit (U.S. Biochem., Cleveland, Ohio) using PCR amplicon (50 ng) with 25-50 ng primers according to manufacturer instructions. A 7% polyacrylamide sequencing gel was utilized in 0.1 M Tris, 0.03 M Taurine and 5 mM EDTA. The gel was electrophoresed at 1,800 V for 1.5 to 3 hours (−50 mAmps), fixed in 10% methanol-10% acetic acid for 15 minutes, transferred to Whatman 3 mM paper and dried in a gel dryer at 80° C. for 1 hour. The dried gel was exposed to x-ray film for 1-3 days. In some cases, automatic DNA sequencing was performed with 10 ng amplicon and 50 ng primer.

Example 4

*Mycobacterium leprae* Specific PCR-RFLP

DNA from skin biopsies of leprosy patients were screened for the presence of *M. leprae* DNA using the RFLP for the heat shock 65 gene (hsp65). 24 paraffin embedded skin tissue samples were collected after a chart review of patients with proven *M. leprae* infection. Table 2 lists source, fite stain, anatomical site, date of biopsy (Bx), histology, clinical diagnosis, age, sex, country of birth, first symptoms (Sx), ethnicity, date entered USA and countries visited when available.

TABLE 2

| Patient | Source | hsp65 | hsp65 PAGE | Fite | Anatomical site | Date of biopsy (Bx) | Histology | Clinical diagnosis |
|---|---|---|---|---|---|---|---|---|
| 1 | Harlem Hosp | Pos | 3 | | | | | |
| 2 | outside | Pos | 2 | | | | | Lepromatous |
| 3 | Lousiana | Pos | 1 | | | March 1999 | | Lepromatous |
| 4 | outside | pos (weak) | 1 | few | Rt arm | Feb. 21, 1997 | BL-BB in regression | Lepromatous |
| 5 | outside | Pos | 3 | numerous | skin | Oct. 1, 2002 | Xanthogranuloma c/w HD | Lepromatous |
| 6 | outside | Pos | | neg | Rt cheek | Oct. 13, 2003 | granulomatous dermatitis, ?HD | Borderline/Dimorph |
| 7 | NYU | Pos | 1 | | | | | Indeterminate |
| 8 | BH | neg (redo) | | | | | | Tuberculous |
| 9 | Lousiana | Pos | 2 | neg | | | | |
| 10 | Lousiana | Pos | 1 | neg | Rt back | Feb. 13, 1997 | chronic infl | LL-BL, regressed |
| 11 | BH | Pos | 2 | numerous | L arm | April 1999 | granulomatous infl | Lepromatous |
| 12 | BH | neg (missing) | | pos | L thigh | july, 2002 | foamy histiocytes, perineural | Lepromatous |

TABLE 2-continued

| | | | | | | | | |
|---|---|---|---|---|---|---|---|---|
| 13 | Brooklyn | | | | | | | Borderline/Dimorph |
| 14 | Puerto Rico | Pos | 3 | numerous | L abd | Apr. 29, 1999 | Lepromatous leprosy | MB |
| 15 | Puerto Rico | Pos | 1 | numerous | back | Feb. 12, 2002 | granulomatous dermatitis | |
| 16 | Puerto Rico | Neg | | numerous | skin | Nov. 24, 1999 | LL-BL | MB |
| 17 | Puerto Rico | Pos | 1 | numerous | skin | Dec. 6, 2002 | sarcoidal granul. Dermatitis | |
| 18 | Puerto Rico | Neg | | ? | | | ? | |
| 19 | Puerto Rico | neg | | numerous | Rt leg | 2-Dec | granulom. Dermat. C/w LL | |
| 20 | Puerto Rico | pos | 1 | numerous | chest | Aug. 4, 2002 | Lepromatous leprosy | MB |
| 21 | Puerto Rico | pos | 3 | pos | skin | Jun. 18, 2003 | Nodular infiltrates of histiocyts | |
| 22 | Puerto Rico | neg | | numerous | skin | May 10, 2001 | Xanthogranuloma | |
| 23 | Dr Weinberg | neg | | | | | | Borderline/Dimorph |
| 24 | | pos | 3 | | | | | Lepromatous |

| Patient | Age | Sex | Born In | 1st symptoms (Sx) | Ethnicity | Entered US | Countries visited |
|---|---|---|---|---|---|---|---|
| 1 | | | | | | | |
| 2 | ,59 | M | D.R. | 65 | Latino | May 1985 | DR, 19 yrs |
| 3 | | M | Long Island | 96, aug | Caucasian | n/a | none |
| 4 | | F | USA | April 1973 | Caucasian | n/a | none |
| 5 | ,31 | M | D.R. | July, 2002 | Hispanic | October, 2002 | D.R., 18 yrs |
| 6 | ,34 | M | Philippines | November 2003 | Asian | April 1994 | Philippines, 23 yrs |
| 7 | ,18 | M | Bangladesh | December, 2003 | Asian | 1993 | Bangladesh, 3 yrs |
| 8 | | F | Columbia | April 1973 | Hispanic | December 1986 | Columbia, 52 yrs |
| 9 | | | | | | | |
| 10 | ,44 | M | Vietnam | March 1982 | Asian | unclear | Vietnam, 21 yrs |
| 11 | ,33 | M | China | January 1998 | Asian | February 1998 | China, ?yrs |
| 12 | ,34 | M | Puerto Rico | 1983 | Hispanic | 1990 | unclear |
| 13 | ,24 | F | Surinam | January, 2004 | Asian | August, 2003 | Surinam, 22 yrs |
| 14 | ,54 | M | P.R. | | | | |
| 15 | ,55 | M | P.R. | | | | |
| 16 | ,34 | M | P.R. | | | | |
| 17 | ,52 | M | P.R | | | | |
| 18 | ,62 | M | P.R. | | | | |
| 19 | ,27 | M | P.R. | | | | |
| 20 | ,31 | M | P.R. | | | | |
| 21 | ,44 | F | P.R. | | | | |
| 22 | | | | | | | |
| 23 | ,37 | M | Philippines | February, 2004 | Asian | april, 1978 | Philippines, 10 yrs |
| 24 | ,25 | M | Ecuador | March: 2004 | Hispanic | January 2000 | Ecuador, 20 yrs |

To confirm the clinical diagnosis and presence of leprosy DNA in the cohort, the *M. leprae* specific PCR-RFLP for the hsp65 gene was used. In FIG. 3, the typical pattern is shown for *M. leprae* found in 5/24 (21%) of patients. In some of the patients, two additional patterns were found. The typical pattern described in *M. leprae* was assigned pattern 3, while variant patterns were assigned 1 and 2. Pattern 1 was found in 7/25 (29%) of patients while pattern 2 was identified in 3/24 (12%) of patients. DNA from 9/24 (38%) patients did not amplify any amplicon. Also shown are the RFLP patterns for *M. tb.* and *M. bovis*. No correlation with any pattern was found between fite staining or geographic location. DNA from all three patterns was sequenced. Pattern 3 contained the exact predicted sequence for the hsp65 gene for *M. leprae* obtained from the *M. leprae* database (genolist.pateur.fr/leproma). Patterns 1 and 2 contained DNA sequence equal to pattern 3 except for the addition of predicted sites for HaeIII which resulted in the variant patterns (data not shown).

To eliminate the possibility that a contaminating mycobacteria in the samples was being amplified and to prove that the novel hsp65 gene patterns were derived from *M. leprae* DNA, other *M. leprae* genes for DNA gyrase A (gyrA) or B (gyrB) or dihydropteroate synthase (folP) were PCR amplified. These genes contain unique *M. leprae* specific polymorphisms (SNPs) that demonstrate that we are amplifying *M. leprae* DNA (Guillemin et al., "Correlation Between Quinolone Susceptibility Patterns and Sequences in the A and B Subunits of DNA Gyrase in Mycobacteria," *Antimicrobial Agents and Chemotherapy* 42:2084-2088 (1998); You et al., Mutations in Genes Related to Drug Resistance in *Mycobacterium leprae* Isolates from Leprosy Patients in Korea," *J. Medicine* 50:6-11 (2005); Maeda et al., "Multidrug Resistant *Mycobacterium leprae* from Patients with Leprosy," *Antimicrobial Agents and Chemotherapy* 45:3636-3639 (2001); and Kim et al., "Detection of Gene Mutations Related with Drug Resistance in *Mycobacterium leprae* from Leprosy Patients Using Touch-Down (TD) PCR," *FEMS Immunology and Medical Microbiology* 36:27-32 (2003), which are hereby incorporated by reference in their entirety). Sequencing of these genes from DNA with the variant hsp65 patterns (patterns 1 and 2) resulted in the identical SNP sequence published for *M. leprae* (Guillemin et al., "Correlation Between Quinolone Susceptibility Patterns and Sequences in the A and B Subunits of DNA Gyrase in Mycobacteria," *Antimicrobial Agents and Chemotherapy* 42:2084-2088 (1998); and Kim et al., "Detection of Gene Mutations Related with Drug Resistance in *Mycobacterium Leprae* from Leprosy Patients Using Touch-Down (TD) PCR," *FEMS Immunology and Medical Microbiology* 36:27-32 (2003), which are hereby incorporated by reference in their entirety).

Until recently, very little methodology and information was available to strain type *Mycobacterium leprae*. Molecular epidemiology techniques examining RFLPs, VNTRs, SNPs, STRs, etc. and the availability of the leprosy genome will enrich this area. Matosuoka et al. (Matsuoka et al., "*Mycobacterium Leprae* Typing by Genomic Diversity and Global Distribution of Genotypes," *International J. Leprosy* 68:121-128 (2000), which is hereby incorporated by reference in its entirety) and Chae et al. (Chae et al., "Typing of Clinical Isolates of *Mycobacterium Leprae* and Their Distribution in Korea," *Leprosy Review* 73:41-46 (2002), which is hereby incorporated by reference in its entirety) reported a 6 bp repeat (GACATC) in the rpoT gene. They found 3 copies in Okinawa Islands, Bangladesh, India, Indonesia, Nepal, Pakistan, Philippines, Brazil and Haiti. Two of 67 Korean isolates had 3 copies. Four copies were found in isolates from Japan (except Okinawa) and Korea (65 of 67 or 97%). In total, there were 120 isolates examined. Eighty-eight (73%) had 4 copies and 32 (27%) had 3 copies. Non-human isolates from armadillo and mangabey monkey had three copies. Shin et al. (Shin et al., "Variable Numbers of TTC Repeats in *Mycobacterium Leprae* DNA from Leprosy Patients and Use in Strain Differentiation," *J. Clinical Microbiology* 38:4535-4538 (2000), which is hereby incorporated by reference in its entirety) identified a VNTR of a TTC triplet in an intergenic region. They found between 10 and 37 copies from 34 isolates. Ten, 13, 22, 32, and 37 copies were only found in one isolate each. Nineteen, 23 and 27 copies were found in two isolates each. Fourteen, 15, 20, 21 and 28 copies were found in 3 isolates each, while 24 and 25 copies were found in 4 isolates each. Truman et al. (Truman et al., "Genotypic Variation and Stability of Four Variable-Number Tandem Repeats and Their Suitability for Discriminating Strains of *Mycobacterium Leprae*," *J. Clinical. Micro* 42:2558-2565 (2004), which is hereby incorporated by reference in its entirety) used four VNTRs to discriminate 12 isolates from different geographic locations. The GAA VNTR had 10-16 copies, the AT17 VNTR had 10-15 copies, the GTA had 9-12 copies and the TA18 had 13-20 copies. The TA18 VNTR was the most polymorphic. Most strains were relatively stable after short term passage in armadillos. Interestingly, long-term expansion generally caused loss in copy number. Groathouse et al. (Groathouse et al., "Multiple Polymorphic Loci for Molecular Typing of Strains of *Mycobacterium Leprae*," *J. Clin. Micro* 42:1666-1672 (2004), which is hereby incorporated by reference in its entirety) using various computer search programs analyzed the *M. leprae* genome for potential VNTR loci. Nine new polymorphic VNTRs were identified in screening DNA from four isolates grown in armadillos. Recently, Monot et al. (Monot et al., "On the Origin of Leprosy," *Science* 308:1040-1042 (2005), which is hereby incorporated by reference in its entirety) identified 4 SNP-types and presented world-wide distribution of these SNP-types. Based upon these SNP-types, they postulated the evolutionary spread of leprosy.

To better understand the transmission, source and course of leprosy, a plan to use molecular epidemiology to screen skin DNA from patients for tandem repeats (VNTRs or STRs) or to develop other methodology was implemented. Initially, for the *M. leprae* specific hsp65 RFLP was screened for patients from various geographic locations. Besides the published pattern, unexpectedly, eight variant patterns that are similar but different to patterns seen in other mycobacteria were found. This proved the RFLPs were not derived from contaminating mycobacteria by amplifying other *M. leprae* genes that contained only SNPs found in *M. leprae*. These variant patterns were found in 10 of 24 patients, were very polymorphic and are ideal for future molecular epidemiology studies.

The mycobacterial heat shock 65 proteins are recognized as major immune targets of mycobacterial diseases and have been reported to co-react with other highly immunogenic proteins (Rambukkana et al., "Identification and Characterization of Epitopes Shared Between the Mycobacterial 65-Kilodalton Heat Shock Protein and the Actively Secreted 85 Complex: Their In Situ Expression of the Cell Wall Surface of *Mycobacterium leprae*," *Infection and Immunity* 60:4517-4527 (1992), which is hereby incorporated by reference in its entirety). Abundant literature supports the chaperonin, adjuvant like effect of Hsp65s from a variety of mycobacteria and the potential therapeutic use of the heat shock 65 proteins for auto-immune (Nomaguchi et al., "Prevention of Diabetes in Non-Obese Ddiabetic Mice by a Single Immunization with *Mycobacterium Leprae*," *Nihon Hansenbyo Gakkai Zasshi* 71:31-8 (2002), Rambukkana et al., "Antibodies to Mycobacterial 65-kDa Heat Shock Protein and Other Immunodominant Antigens in Patients with Psoriasis," *J. Invest, Derm* 100:87-92 (1993), which are hereby incorporated by reference in their entirety), viral (Neefe et al., "CoVal Fusions: A Therapeutic Vaccine Platform Using Heat Shock Proteins to Treat Chronic Viral Infections and Cancer," *Dev. Biol* 116:193-200 (2004), which is hereby incorporated by reference in its entirety), cancer (Neefe et al., "CoVal Fusions: A Therapeutic Vaccine Platform Using Heat Shock Proteins to Treat Chronic Viral infections and Cancer," *Dev. Biol* 116:193-200 (2004), which is hereby incorporated by reference in its entirety), atherosclerosis (Ghayour-Mobarhan et al., "Heat Shock Protein Antibody Titers are Reduced by Statin Therapy in Dyslipidernic Subjects: A Pilot Study," *Angiology* 56:61-68 (2005), which is hereby incorporated by reference in its entirety) and in even vaccine development (Sbai et al., "Use of T Cell Epitopes for Vaccine Development Current Drug Targets Infect," *Discord* 1:303-13 (2001), which is hereby incorporated by reference in its entirety). While heat shock proteins in this molecular weight range are highly conserved and significant cross-reactivity between mammalian and microbes as diverse as *E. coli* and various mycobacteria is known to exist, some degree of specificity has been demonstrated. For example, studies have shown the heat shock 65 protein of *M. leprae* can selectively ameliorate asthma in a murine model (Rha et al., "Effect of Microbial Heat Shock Proteins on Airway Inflammation and Hyperresponsiveness," *J. Immunology* 169:5300-7 (2002), which is hereby incorporated by reference in its entirety). The finding of eight additional polymorphic forms of *M. leprae* Hsp65 could have profound implications for the therapeutic use of heat shock proteins and provide a repertoire to avoid resistance.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. An expression vector comprising an isolated polynucleotide encoding a heat shock protein operatively linked to a promoter, said heat shock protein having the amino acid sequence of SEQ ID NO: 3 and being heterologous to the remainder of the expression vector.

2. The expression vector according to claim 1, wherein the polynucleotide has the nucleotide sequence of SEQ ID NO: 4.

3. An isolated host cell comprising the expression vector of claim 1.

4. The expression vector according to claim 1, wherein the polynucleotide encodes a heat shock protein is fused to a polynucleotide encoding an antigen selected from the group consisting of Papillomavirus antigen, herpes simplex virus antigen, hepatitis B virus antigen, hepatitis C virus antigen, cytomegalovirus antigen, Epstein-Barr virus antigen, influenza virus antigen, measles virus antigen, human immunodeficiency virus antigen, bacterial antigen, mycoplasma antigen, mycobacterial antigen, fungus antigen, protozoan antigen, and a tumor-associated antigen.

5. An isolated host cell comprising the expression vector of claim 4.

6. The expression vector according to claim 4, wherein the polynucleotide comprises the nucleotide sequence of SEQ ID NO: 4.

7. An isolated host cell comprising the expression vector of claim 6.

* * * * *

UNITED STATES PATENT AND TRADEMARK OFFICE

CERTIFICATE OF CORRECTION

PATENT NO. : 8,835,619 B2
APPLICATION NO. : 12/624288
DATED : September 16, 2014
INVENTOR(S) : William R. Levis et al.

It is certified that error appears in the above-identified patent and that said Letters Patent is hereby corrected as shown below:

On the Title page, under the Related U.S. Application Data heading at item (62), please delete "Sep. 29, 2006" and replace with "Sep. 19, 2006".

Signed and Sealed this
Tenth Day of February, 2015

Michelle K. Lee
*Deputy Director of the United States Patent and Trademark Office*

SEQUENCE LISTING

<160> NUMBER OF SEQ ID NOS: 34

<210> SEQ ID NO 1
<211> LENGTH: 113
<212> TYPE: PRT
<213> ORGANISM: Mycobacterium leprae

<400> SEQUENCE: 1

```
Glu Lys Ile Gly Ala Glu Leu Val Lys Glu Val Ala Lys Lys Thr Asp
  1               5                  10                  15

Asp Val Ala Gly Asp Gly Thr Thr Thr Ala Thr Val Leu Ala Gln Ala
             20                  25                  30

Leu Val Lys Glu Gly Leu Arg Asn Val Ala Ala Gly Ala Asn Pro Leu
         35                  40                  45

Gly Leu Lys Arg Gly Ile Glu Lys Ala Val Asp Lys Ile Thr Gln Thr
     50                  55                  60

Leu Leu Asp Ser Ala Lys Asp Val Glu Thr Lys Glu Gln Ile Ala Ala
 65                  70                  75                  80

Thr Ala Ser Ile Ser Ala Gly Asp Gln Ser Ile Gly Asp Leu Ile Ala
                 85                  90                  95

Glu Ala Lys Asp Lys Val Gly Asn Glu Gly Val Ile Thr Val Glu Glu
            100                 105                 110

Ser
```

<210> SEQ ID NO 2
<211> LENGTH: 339
<212> TYPE: DNA
<213> ORGANISM: Mycobacterium leprae

<400> SEQUENCE: 2

```
gagaagatcg gcgccgagct ggtcaaggaa gtcgccaaga agaccgacga cgtcgccggt      60

gacggcacca cgacggccac cgtgctggcc caggccctgg tcaaagaggg tctgcgtaac     120

gttgctgcgg gcgccaaccc actgggtctg aagcgcggca tcgagaaggc cgtcgataag     180

atcacccaga cgctgctgga ctcggccaag gacgtcgaga ccaaggagca gatcgcagcc     240

accgctagca tttctgccgg tgaccagtcg atcggcgacc tgatcgccga agcgaaggac     300

aaggtcggca acgagggcgt catcaccgtc gaggagtcc                            339
```

<210> SEQ ID NO 3
<211> LENGTH: 113
<212> TYPE: PRT
<213> ORGANISM: Mycobacterium leprae

<400> SEQUENCE: 3

```
Glu Lys Ile Gly Ala Glu Leu Val Lys Glu Val Ala Lys Lys Thr Asp
  1               5                  10                  15

Asp Val Ala Gly Asp Gly Thr Thr Thr Ala Thr Val Leu Ala Gln Ala
             20                  25                  30

Leu Val Arg Glu Gly Leu Arg Asn Val Ala Ala Gly Ala Asn Pro Leu
         35                  40                  45

Gly Leu Lys Arg Gly Ile Glu Lys Ala Val Gly Lys Ile Thr Glu Val
     50                  55                  60

Leu Leu Ser Ser Ala Lys Asp Val Glu Thr Lys Glu Gln Ile Ala Ala
 65                  70                  75                  80

Thr Ala Gly Ile Ser Ala Gly Asp Gln Ser Ile Gly Asp Leu Ile Ala
                 85                  90                  95
```

-continued

Val Ala Met Asp Lys Val Gly Asn Glu Gly Ile Ile Thr Val Glu Glu
100 105 110

Ser

<210> SEQ ID NO 4
<211> LENGTH: 339
<212> TYPE: DNA
<213> ORGANISM: Mycobacterium leprae

<400> SEQUENCE: 4
gagacgatcg gcgccgagct ggtcaaggaa gtcgccaaga agaccgacga cgtcgccggt 60
gacggcacga cgacggccac ggtgctcgcc caggcgttgg tccgcgaggg cctgcgcaac 120
gtcgcggctg gcgccaaccc gctgggtctc aagcgcggca tcgagaaggc cgttggaaaa 180
atcacggaag ttctcctgtc gtcggccaag gacgtcgaga ccaaggagca gatcgctgcc 240
accgctggca tttctgccgg tgaccagtcg atcggcgacc tgatcgccgt agcgatggac 300
aaggtcggca acgagggcat catcaccgtc gaggagtcc 339

<210> SEQ ID NO 5
<211> LENGTH: 113
<212> TYPE: PRT
<213> ORGANISM: Mycobacterium leprae

<400> SEQUENCE: 5

Glu Lys Ile Gly Ala Glu Leu Val Lys Glu Val Ala Lys Lys Thr Asp
1 5 10 15

Asp Val Ala Gly Asp Gly Thr Thr Thr Ala Thr Val Leu Ala Gln Ala
20 25 30

Leu Val Lys Glu Gly Leu Arg Asn Val Ala Ala Gly Ala Asn Pro Leu
35 40 45

Gly Leu Lys Arg Gly Ile Glu Lys Ala Val Asp Lys Ile Thr Gln Thr
50 55 60

Leu Leu Asp Ser Ala Lys Asp Val Glu Thr Lys Glu Gln Ile Ala Ala
65 70 75 80

Thr Ala Ala Ile Ser Ala Gly Asp Gln Ser Ile Gly Asp Leu Ile Ala
85 90 95

Glu Ala Met Asp Lys Val Gly Asn Glu Gly Val Ile Thr Val Glu Glu
100 105 110

Ser

<210> SEQ ID NO 6
<211> LENGTH: 339
<212> TYPE: DNA
<213> ORGANISM: Mycobacterium leprae

<400> SEQUENCE: 6
gagaagatcg gcgccgagct ggtcaaggaa gtcgccaaga agaccgacga cgtcgccggt 60
gacggcacca cgacggccac cgtgctggcc caggccctgg ttaaagaggg tctgcgtaac 120
gttgctgcgg gcgccaaccc gctgggtctg aagcgcggca tcgagaaggc cgtcgataag 180
atcacccaga cgctgctgga ctcggccaag gacgtcgaga ccaaggagca gatcgctgcc 240
accgcggcca tctccgcggg cgaccagtct atcggcgacc tgatcgccga ggcgatggac 300
aaggtcggca acgagggcgt catcaccgtc gaggagtcc 339

<210> SEQ ID NO 7
<211> LENGTH: 112

<212> TYPE: PRT
<213> ORGANISM: Mycobacterium leprae

<400> SEQUENCE: 7

```
Glu Lys Ile Gly Ala Glu Leu Val Lys Glu Val Ala Lys Lys Thr Asp
  1               5                  10                  15

Asp Val Ala Gly Asp Gly Thr Thr Thr Ala Thr Val Leu Ala Gln Ala
             20                  25                  30

Leu Val Lys Glu Gly Leu Arg Asn Val Ala Ala Gly Ala Asn Pro Leu
         35                  40                  45

Gly Leu Lys Arg Gly Ile Glu Lys Ala Val Asp Lys Ile Thr Gln Thr
     50                  55                  60

Leu Leu Asp Ser Ala Glu Asp Val Glu Thr Lys Glu Gln Ile Ala Ala
 65                  70                  75                  80

Thr Ala Gly Ile Pro Ala Gly Asp Gln Ser Ile Gly Asp Leu Ile Ala
                 85                  90                  95

Glu Ala Met Asp Lys Val Gly Asn Gly Ala Ser Ser Pro Ser Arg Ser
            100                 105                 110
```

<210> SEQ ID NO 8
<211> LENGTH: 338
<212> TYPE: DNA
<213> ORGANISM: Mycobacterium leprae

<400> SEQUENCE: 8

```
gagaagatcg gcgccgagct ggtcaaggaa gtcgccaaga agaccgacga cgtcgccggt      60

gacggcacga cgacggccac ggttctggcc caggccttgg tccgcgaggg cctgcgtaac     120

gtcgccgccg gcgccaaccc gctgggtctg aagcgcggca tcgagaaggc cgtcgataag     180

atcacccaga cgctgctgga ctcggccgag gacgtcgaga ccaaggagca gatcgctgcc     240

accgctggca ttcctgccgg tgaccagtcg atcggcgacc tgatcgccga agcgatggac     300

aaggtcggca acggggcgtc atcaccgtcg aggagtcc                             338
```

<210> SEQ ID NO 9
<211> LENGTH: 113
<212> TYPE: PRT
<213> ORGANISM: Mycobacterium leprae

<400> SEQUENCE: 9

```
Glu Lys Ile Gly Ala Glu Leu Val Lys Glu Val Ala Lys Lys Thr Asp
  1               5                  10                  15

Asp Val Ala Gly Asp Gly Thr Thr Thr Ala Thr Val Leu Ala Gln Ala
             20                  25                  30

Leu Val Lys Glu Gly Leu Arg Asn Val Ala Ala Gly Ala Asn Pro Leu
         35                  40                  45

Gly Leu Lys Arg Gly Ile Glu Lys Ala Val Asp Lys Ile Thr Gln Thr
     50                  55                  60

Leu Leu Asp Pro Ala Lys Asp Val Glu Thr Lys Glu Gln Ile Ala Ala
 65                  70                  75                  80

Thr Ala Gly Thr Ser Ala Gly Asp Gln Ser Ile Gly Asp Pro Ile Ala
                 85                  90                  95

Glu Ala Met Asp Gly Val Gly Asn Glu Gly Val Ile Thr Val Glu Glu
            100                 105                 110

Ser
```

<210> SEQ ID NO 10

-continued

<211> LENGTH: 339
<212> TYPE: DNA
<213> ORGANISM: Mycobacterium leprae

<400> SEQUENCE: 10
gagaagatcg gcgccgagct ggtcaaggaa gtcgccaaga agaccgacga cgtcgccggt 60
gacggcacca cggcggccac cgtgctggcc caggccctgg tcaaagaggg tctgcgtaac 120
gttgctgcgg gcgccaaccc gctgggtctg aagcgcggca tcgagaaggc cgtcgataag 180
atcacccaga cgctgctgga cccggccaag gacgtcgaga ccaaggagca gatcgctgcc 240
accgctggca catcagccgg tgaccagtcg atcggcgacc cgatcgccga agcgatggac 300
gaggtcggca acgagggcgt catcaccgtc gaggagtcc 339

<210> SEQ ID NO 11
<211> LENGTH: 113
<212> TYPE: PRT
<213> ORGANISM: Mycobacterium leprae

<400> SEQUENCE: 11

Glu Lys Ile Gly Ala Glu Leu Val Lys Glu Val Ala Lys Lys Thr Asp
1 5 10 15

Glu Val Ala Cys Asp Gly Thr Thr Thr Ala Thr Val Leu Ala Gln Ala
20 25 30

Leu Val Arg Glu Gly Leu Arg Asn Val Ala Ala Gly Ala Asp Pro Leu
35 40 45

Ser Leu Lys Arg Gly Ile Glu Lys Ala Val Ala Ala Val Thr Glu Gln
50 55 60

Leu Leu Ala Ser Ala Lys Glu Val Glu Thr Lys Glu Ala Ile Ala Ala
65 70 75 80

Thr Ala Ser Ile Ser Ala Ala Asp Thr Gln Ile Gly Ala Leu Ile Ala
85 90 95

Glu Ala Leu Asp Lys Val Gly Lys Glu Gly Val Ile Thr Val Glu Glu
100 105 110

Ser

<210> SEQ ID NO 12
<211> LENGTH: 339
<212> TYPE: DNA
<213> ORGANISM: Mycobacterium leprae

<400> SEQUENCE: 12
gagaagatcg gcgccgagct ggtcaaggaa gtcgccaaga agactgacga agtcgcctgc 60
gacggtacca ccaccgctac cgttctggcc caggccttgg ttcgcgaagg cttgcgcaac 120
gtcgcagccg gcgctgatcc gctgagcctc aagcgcggca tcgagaaggc tgtcgccgcg 180
gtgaccgagc agctgctggc ttccgccaag gaagtcgaga ccaaagaaga gatcgcggcc 240
actgcttcga tctccgccgc ggacacccag atcggcgcgt tgatcgccga agccctggac 300
aaggtcggca aagaaggcgt catcacggtc gaagagtcc 339

<210> SEQ ID NO 13
<211> LENGTH: 74
<212> TYPE: PRT
<213> ORGANISM: Mycobacterium leprae

<400> SEQUENCE: 13

Glu Lys Ile Gly Ala Glu Leu Val Lys Glu Ala Ala Lys Lys Thr Asp
1 5 10 15

-continued

```
Glu Val Ala Gly Asp Gly Thr Thr Thr Ala Thr Val Leu Ala Gln Ala
            20                  25                  30

Leu Val Arg Glu Gly Leu Arg Asn Val Ala Ala Gly Ala Asp Pro Leu
        35                  40                  45

Ser Leu Lys Arg Gly Ile Glu Lys Ala Val Ala Ala Val Thr Glu Gln
    50                  55                  60

Leu Leu Ala Ser Ala Lys Glu Val Glu Thr
65                  70
```

<210> SEQ ID NO 14
<211> LENGTH: 339
<212> TYPE: DNA
<213> ORGANISM: Mycobacterium leprae

<400> SEQUENCE: 14

```
gagaagatcg gcgccgagct ggtcaaggaa gccgccaaga agactgacga agtcgccggc      60

gacggtacca ccaccgctac cgttctggcc caggccttgg ttcgcgaagg cttgcgcaac     120

gtcgcagccg gcgctgatcc gctgagcctc aagcgcggca tcgagaaggc tgtcgccgcg     180

gtgaccgagc agctgctggc ttccgccaag gaagtcgaga cctaagaaga gatcgcggcc     240

actgcttcga tctccgccgc ggacacccag atcggcgcgt tgatcgccga agccctggac     300

aaggtcggca aagaaggcgt catcacggtc gaagagtcc                           339
```

<210> SEQ ID NO 15
<211> LENGTH: 100
<212> TYPE: PRT
<213> ORGANISM: Mycobacterium leprae

<400> SEQUENCE: 15

```
Glu Lys Ile Gly Ala Glu Leu Val Lys Glu Val Ala Lys Lys Thr Asp
1               5                   10                  15

Glu Val Ala Gly Asp Gly Thr Thr Thr Ala Thr Val Leu Ala Gln Ala
            20                  25                  30

Leu Asp Arg Glu Gly Leu Arg Asn Val Ala Ala Gly Ala Asp Pro Leu
        35                  40                  45

Ser Leu Lys Arg Gly Ile Glu Lys Ala Val Ala Ala Val Thr Glu Gln
    50                  55                  60

Leu Leu Ala Ser Ala Lys Glu Val Glu Thr Lys Glu Glu Ile Ala Ala
65                  70                  75                  80

Thr Ala Ser Ile Ser Ala Ala Asp Thr Gln Ile Gly Ala Leu Ile Ala
                85                  90                  95

Glu Ala Leu Asp
            100
```

<210> SEQ ID NO 16
<211> LENGTH: 339
<212> TYPE: DNA
<213> ORGANISM: Mycobacterium leprae

<400> SEQUENCE: 16

```
gaggagatcg gcgccgagct ggtcaaggaa gtcgccaaga agactgacga agtcgccggc      60

gacggtacca ccaccgctac cgttctggcc caggccttgg atcgcgaagg cttgcgcaac     120

gtcgcagccg gcgctgatcc gctgagcctc aagcgcggca tcgagaaggc tgtcgccgcg     180

gtgaccgagc agctgctggc ttccgccaag gaagtcgaga ccaaagaaga gatcgcggcc     240

actgcttcga tctccgccgc ggacacccag atcggcgcgt tgatcgccga agccctggac     300
```

taggtcggca aagaaggcgt catcacggtc gaagagtcc 339

<210> SEQ ID NO 17
<211> LENGTH: 103
<212> TYPE: PRT
<213> ORGANISM: Mycobacterium leprae

<400> SEQUENCE: 17

Glu Lys Ile Gly Ala Glu Leu Val Lys Glu Val Ala Lys Lys Thr Asp
1 5 10 15

Asp Val Ala Gly Asp Gly Thr Thr Thr Ala Thr Val Leu Ala Gln Ala
20 25 30

Leu Val Lys Glu Gly Leu Arg Asn Val Ala Ala Gly Ala Asn Pro Leu
35 40 45

Gly Leu Lys Arg Gly Ile Glu Lys Ala Val Asp Lys Val Thr Glu Thr
50 55 60

Leu Glu Gln Ile Ala Ala Thr Ala Ala Ile Ser Ala Gly Asp Gln Ser
65 70 75 80

Ile Gly Asp Leu Ile Ala Glu Ala Met Asp Lys Val Gly Asn Glu Gly
85 90 95

Val Ile Thr Val Glu Glu Ser
100

<210> SEQ ID NO 18
<211> LENGTH: 339
<212> TYPE: DNA
<213> ORGANISM: Mycobacterium leprae

<400> SEQUENCE: 18
gagaagattg gcgctgagtt ggtcaaggaa gtcgccaaga agacagatga cgtcgccggt 60
gatggcacca cgacggccac cgtgctggcc caggcattgg tcaaagaggg cctacgcaac 120
gtcgcggccg gcgccaaccc gctaggtctc aagcgtggca tcgagaaagc tgtcgataag 180
gtaactgaga ctctgctcaa ggacgctaag gaggtcgaaa ccaaggaaca aattgctgcc 240
actgcagcga tttcggcggg tgaccagtcg atcggtgatc tgatcgccga ggcgatggac 300
aaggttggca acgagggtgt tatcaccgtc gaggaatcc 339

<210> SEQ ID NO 19
<211> LENGTH: 22
<212> TYPE: DNA
<213> ORGANISM: Mycobacterium leprae

<400> SEQUENCE: 19
caccaacgat ggtgtccatc gc 22

<210> SEQ ID NO 20
<211> LENGTH: 21
<212> TYPE: DNA
<213> ORGANISM: Mycobacterium leprae

<400> SEQUENCE: 20
cttgtcgaac cgcataccct c 21

<210> SEQ ID NO 21
<211> LENGTH: 25
<212> TYPE: DNA
<213> ORGANISM: Mycobacterium leprae

<400> SEQUENCE: 21

-continued aggagatcga gctggaggat ccgta 25

<210> SEQ ID NO 22
<211> LENGTH: 22
<212> TYPE: DNA
<213> ORGANISM: Mycobacterium leprae

<400> SEQUENCE: 22
gagctgcagc ccaaaggtgt tg 22

<210> SEQ ID NO 23
<211> LENGTH: 30
<212> TYPE: DNA
<213> ORGANISM: Mycobacterium leprae

<400> SEQUENCE: 23
cccgtgcaac atcagcgcgc gtagtatcga 30

<210> SEQ ID NO 24
<211> LENGTH: 30
<212> TYPE: DNA
<213> ORGANISM: Mycobacterium leprae

<400> SEQUENCE: 24
actgacaatt cgttctcaga tggcggacgt 30

<210> SEQ ID NO 25
<211> LENGTH: 24
<212> TYPE: DNA
<213> ORGANISM: Mycobacterium leprae

<400> SEQUENCE: 25
tacttactgt aatcccctgt gctg 24

<210> SEQ ID NO 26
<211> LENGTH: 20
<212> TYPE: DNA
<213> ORGANISM: Mycobacterium leprae

<400> SEQUENCE: 26
ttgatcctga cgatgctgtc 20

<210> SEQ ID NO 27
<211> LENGTH: 30
<212> TYPE: DNA
<213> ORGANISM: Mycobacterium leprae

<400> SEQUENCE: 27
gtcgggtctt gtacgcgatg ttagactccg 30

<210> SEQ ID NO 28
<211> LENGTH: 30
<212> TYPE: DNA
<213> ORGANISM: Mycobacterium leprae

<400> SEQUENCE: 28
caacctcacc aaggaatttc ctgacacaca 30

<210> SEQ ID NO 29
<211> LENGTH: 24
<212> TYPE: DNA
<213> ORGANISM: Mycobacterium leprae -continued

```
<400> SEQUENCE: 29

cccggaccgt agccacgcta agtc                                          24


<210> SEQ ID NO 30
<211> LENGTH: 22
<212> TYPE: DNA
<213> ORGANISM: Mycobacterium leprae

<400> SEQUENCE: 30

catcgctgcc ggtgggtcat ta                                            22


<210> SEQ ID NO 31
<211> LENGTH: 31
<212> TYPE: DNA
<213> ORGANISM: Mycobacterium leprae

<400> SEQUENCE: 31

ttggtggact tcctggaaaa acttgccgat t                                  31


<210> SEQ ID NO 32
<211> LENGTH: 30
<212> TYPE: DNA
<213> ORGANISM: Mycobacterium leprae

<400> SEQUENCE: 32

cctggagata tcgaattcat catggattcc                                    30


<210> SEQ ID NO 33
<211> LENGTH: 24
<212> TYPE: DNA
<213> ORGANISM: Mycobacterium leprae

<400> SEQUENCE: 33

actgatcctc gaagttctga actg                                          24


<210> SEQ ID NO 34
<211> LENGTH: 23
<212> TYPE: DNA
<213> ORGANISM: Mycobacterium leprae

<400> SEQUENCE: 34

caatgccgta ataattgctt gaa                                           23
```